United States Patent
Friberg et al.

(10) Patent No.: US 9,132,199 B2
(45) Date of Patent: Sep. 15, 2015

(54) REVERSE THERMAL GELS AND USES THEREFOR

(75) Inventors: Thomas R. Friberg, Pittsburgh, PA (US); Daewon Park, Pittsburgh, PA (US); Yadong Wang, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/581,518

(22) PCT Filed: Mar. 4, 2011

(86) PCT No.: PCT/US2011/027233
§ 371 (c)(1),
(2), (4) Date: Dec. 10, 2012

(87) PCT Pub. No.: WO2011/109732
PCT Pub. Date: Sep. 9, 2011

(65) Prior Publication Data
US 2013/0129663 A1  May 23, 2013

Related U.S. Application Data

(60) Provisional application No. 61/310,874, filed on Mar. 5, 2010, provisional application No. 61/389,491, filed on Oct. 4, 2010, provisional application No. 61/426,514, filed on Dec. 23, 2010.

(51) Int. Cl.
| | |
|---|---|
| A61K 47/48 | (2006.01) |
| C08G 18/83 | (2006.01) |
| A61K 9/00 | (2006.01) |
| A61K 9/06 | (2006.01) |
| A61K 47/34 | (2006.01) |

(52) U.S. Cl.
CPC ......... *A61K 47/48215* (2013.01); *A61K 9/0024* (2013.01); *A61K 9/0051* (2013.01); *A61K 9/06* (2013.01); *A61K 47/34* (2013.01); *A61K 47/482* (2013.01); *A61K 47/48176* (2013.01); *A61K 47/48192* (2013.01); *A61K 47/48784* (2013.01); *C08G 18/833* (2013.01)

(58) Field of Classification Search
None
See application file for complete search history.

(56) References Cited

U.S. PATENT DOCUMENTS

| | | | |
|---|---|---|---|
| 6,004,573 A | 12/1999 | Rathi et al. | |
| 6,306,821 B1 * | 10/2001 | Mikos et al. | 514/8.2 |
| 6,316,011 B1 | 11/2001 | Ron et al. | |
| 6,451,346 B1 * | 9/2002 | Shah et al. | 424/486 |
| 6,541,033 B1 | 4/2003 | Shah | |
| 6,863,859 B2 * | 3/2005 | Levy | 264/401 |
| 2006/0280718 A1 * | 12/2006 | Roy et al. | 424/78.3 |
| 2008/0274190 A1 | 11/2008 | Lee et al. | |

OTHER PUBLICATIONS

Sartori et al. Euro Cells and Materials. vol. 14. Suppl. 3. 2007. p. 18.*
Akdemir et al., Photopolymerized Injectable RGD-Modified Fumarated Poly(ethylene glycol) Diglycidyl Ether Hydrogels for Cell Growth, Macromol. Biosci., 2008, pp. 852-862, vol. 8.
Alferiev et al., Prevention of polyurethane valve cusp calcification with covalently attached bisphosphonate diethylamino moieties, Wiley Periodicals, Oct. 2, 2002, pp. 385-395.
Barakat et al., VEGF inhibitors for the treatment of neovascular age-related macular degeneration, Informa Healthcare Expert Opinion, 2009, pp. 637-646.
Burdick et al., Stimulation of neurite outgrowth by neurotrophins delivered from degradable hydrogels, Biomaterials, 2006 pp. 452-459, vol. 27.
Chappelow et al., Neovascular Age-Related Macular Degeneration, Drugs, 2008, pp. 1029-1036, vol. 68, No. 8.
Chen et al., Preparation and evaluation of thermo-reversible copolymer hydrogels containing chitosan and hyaluronic acid as injectable cell carriers, Polymer, 2009 pp. 107-116, vol. 50.
Choi et al., Thermoreversible Gelation of Poly(ethylene oxide) Biodegradable Polyester Block Copolymers. II, Journal of Polymer Science: Part A: Polymer Chemistry, 1999, pp. 2207-2218, vol. 37.
Christenson et al., Oxidative mechanisms of poly(carbonate urethane) and poly(ether urethane) biodegradation: In vivo and in vitro correlations, Wiley InterScience, Jun. 2, 2004, pp. 245-255.
Christenson et al., Enzymatic degradation of poly(ether urethane) and poly(carbonate urethane) by cholesterol esterase, Biomaterials, 2006 pp. 3920-3926, vol. 27.
Chun et al., The use of injectable, thermosensitive poly(organophosphazene)—RGD conjugates for the enhancement of mesenchymal stem cell osteogenic differentiation, Biomaterials, 2009, pp. 6295-6308, vol. 30.
Cohn et al., PEO-PPO-PEO-based poly(ether ester urethane)s as degradable reverse thermo-responsive multiblock copolymers, Biomaterials, 2006, pp. 1718-1727, vol. 27.
Dayananda et al., pH—and temperature-sensitive multiblock copolymer hydrogels composed of poly(ethylene glycol) and poly(amino urethane), Polymer, 2008, pp. 4968-4973, vol. 49.
D'Errico et al., Structural and Mechanical Properties of UV-Photo-Cross-Linked Poly(N-vinyl-2-pyrrolidone) Hydrogels, Biomacromolecules, 2008, pp. 231-240, vol. 9.
Eglin et al., Farsenol-modified biodegradable polyurethanes for cartilage tissue engineering, Journal of Biomedical Materials Research Part A, Feb. 3, 2009, pp. 393-408, vol. 92A.
Fairbanks et al., Photoinitiated polymerization of PEG-diacrylate with lithium phenyl-2, 4, 6- trimethylbenzoylphosphinate: polymerization rate and cytocompatibility, Biomaterials, 2009, pp. 6702-6707, vol. 30.

(Continued)

Primary Examiner — Amber D Steele
Assistant Examiner — Schuyler Milton
(74) Attorney, Agent, or Firm — The Webb Law Firm

(57) ABSTRACT

Biodegradable triblock copolymer compositions are provided which are useful in tissue engineering and drug delivery. The copolymers are reverse thermal gels in that when heated from a lower temperature to a higher temperature, they gel. These gels are useful in drug delivery when complexed with an active agent. For example the compositions can be used for intraocular injection of active agents, such as anti-angiogenic agents for treatment of a maculopathy or retinitis.

33 Claims, 14 Drawing Sheets

(56) References Cited

OTHER PUBLICATIONS

Gao et al., A neuroinductive biomaterial based on dopamine, PNAS, Nov. 7, 2006, pp. 16681-16686, vol. 103, No. 45.

Gorna et al., Preparation, degradation, and calcification of biodegradable polyurethane foams for bone graft substitutes, Journal of Biomedical Materials Research Part A, May 2, 2003, pp. 813-827.

Gou et al., A novel injectable local hydrophobic drug delivery system: Biodegradable nanoparticles in thermo-sensitive hydrogel, International Journal of Pharmaceutics, 2008, pp. 228-233, vol. 359.

Hacker et al., Synthesis and Characterization of Injectable, Thermally and Chemically Gelable, Amphiphilic Poly(N-isopropylacrylamide)-Based Macromers, Biomacromolecules, 2008, pp. 1558-1570, vol. 9.

He et al., In situ gelling stimuli-sensitive block copolymer hydrogels for drug delivery, Journal of Controlled Release, 2008, pp. 189-207, vol. 127.

Heller et al., Patterned networks of mouse hippocampal neurons on peptide-coated gold surfaces, Biomaterials, 2005, pp. 883-889, vol. 26.

Hiratani et al., Ocular release of timolol from molecularly imprinted soft contact lenses, Biomaterials, 2005, pp. 1293-1298, vol. 26.

Hou et al., In situ Gelling Hydrogels Incorporating Microparticles as Drug Delivery Carriers for Regenerative Medicine, Journal of Pharmaceutical Sciences, Sep. 2008, pp. 3972-3980, vol. 97, No. 9.

Huynh et al., Functionalized injectable hydrogels for controlled insulin delivery, Biomaterials, 2008, pp. 2527-2534, vol. 29.

ISO Inside, Biological evaluation of medical devices—Part 5: Tests for in vitro cytotoxicity, NSAI Standards Irish Standard I.S. EN ISO 10993-5, 2009, 16 pages.

Jeong et al., Biodegradable block copolymers as injectable drug-delivery systems, Nature, Aug. 28, 1997, pp. 860-862, vol. 388.

Jeong et al., Thermoreversible Gelation of Poly(Ethylene Oxide) Biodegradable Polyester Block Copolymers, Journal of Polymer Science: Part A: Polymer Chemistry, 1999, pp. 751-760, vol. 37.

Jeong et al., Thermosensitive sol-gel reversible hydrogels, Advanced Drug Delivery Reviews, 2002, pp. 37-51, vol. 54.

Jo et al., Reverse Thermal Gelation of Aliphatically Modified Biodegradable Triblock Copolymers, Macromol. Biosci., 2006, pp. 923-928, vol. 6.

Johnston et al., Sustained Delivery of Interleukin-2 from a Poloxamer 407 Gel Matrix Following Intraperitoneal Injection in Mice, Pharmaceutical Research, 1992, pp. 425-434, vol. 9, No. 3.

Jun et al., In situ Gel Forming Stereocomplex Composed of Four-Arm PEG-PDLA and PEG-PLLA Block Copolymers, Macromolecular Research, 2008, pp. 704-710, vol. 16, No. 8.

Justin et al., Characterization of Electroconductive Blends of Poly(HEMA-co-PEGMA-co-HMMA-co-SPMA) and Poly (Py-co-PyBA), Biomacromolecules, 2009, pp. 2539-2549, vol. 10.

Khorasani et al., Fabrication of Microporous Thermoplastic Polyurethane for Use as Small-Diameter Vascular Graft Material. I. Phase-Inversion Method, Wiley InterScience, Sep. 13, 2005, pp. 41-48.

Kim et al., Reverse Thermal Gelling PEG-PTMC Diblock Copolymer Aqueous Solution, Macromolecules, 2007, pp. 5519-5525, vol. 40.

Kim et al., Injectable in Situ-Forming pH/Thermo-Sensitive Hydrogel for Bone Tissue Engineering, Tissue Engineering: Part A, 2009, pp. 923-933, vol. 15, No. 4.

Lee et al., Novel Thermoreversible Gelation of Biodegradable PLGA-block-PEO-block-PLGA Triblock Copolymers in Aqueous Solution, Macromol. Rapid Commun., 2001, pp. 587-592, vol. 22.

Lee et al., Thermo-sensitive, injectable, and tissue adhesive sol-gel transition hyaluronic acid/pluronic composite hydrogels prepared from bio-inspired catechol-thiol reaction, Soft Matter, 2010, pp. 977-983, vol. 6.

Lin et al., Functional PEG-peptide hydrogels to modulate local inflammation induced by the pro-inflammatory cytokine TNFα, Biomaterials, 2009, pp. 4907-4914, vol. 30.

Lu et al., Pharmacokinetic Studies of Methotrexate in Plasma and Synovial Fluid Following IV Bolus and Topical Routes of Administration in Dogs, Pharmaceutical Research, 1995, pp. 1474-1477, vol. 12., No. 10.

Mahoney et al., Three-dimensional growth and function of neural tissue in degradable polyethylene glycol hydrogels, Biomaterials, 2006, pp. 2265-2274, vol. 27.

Mann et al., Smooth muscle cell growth in photopolymerized hydrogels with cell adhesive and proteolytically degradable domains: synthetic ECM analogs for tissue engineering, Biomaterials, 2001, pp. 3045-3051, vol. 22.

Mann et al., Tethered-TGF-β increases extracellular matrix production of vascular smooth muscle cells, Biomaterials, 2001, pp. 439-444, vol. 22.

Matsuda et al., A Polyurethane Vascular Access Graft and a Hybrid Polytetrafluoroethylene Graft as an Arterirvenous Fistula for Hemodialysis: Comparison with an Expanded Polytetrafluoroethylene Graft, Artifical Organs, 2003, pp. 722-727, vol. 27, No. 8.

McBane et al., The interaction between hydrolytic and oxidative pathways in macrophage-mediated polyurethane degradation, Wiley InterScience, Mar. 2, 2007, pp. 984-994.

McLemore et al., Controlling Delivery Properties of a Waterborne, In-Situ-Forming Biomaterial, Wiley InterScience, Apr. 28, 2006, pp. 398-410.

Miller et al., Bioactive hydrogels made from step-growth derived PEG-peptide macromers, Biomaterials, 2010, pp. 3736-3743, vol. 31.

Nguyen et al., Injectable Poly(amidoamine)-poly(ethylene glycol)-poly(amidoamine) Triblock Copolymer Hydrogel with Dual Sensitivities: pH and Temperature, Biomacromolecules, 2009, pp. 728-731, vol. 10.

Obara et al., Controlled release of paclitaxel from photocrosslinked chitosan hydrogels and its subsequent effect on subcutaneous tumor growth in mice, Journal of Controlled Release, 2005, pp. 79-89, vol. 110.

Ogura et al., Preparation and Solution Behavior of a Thermoresponsive Diblock Copolymer of Poly(ethyl glycidyl ether) and Poly(ethylene oxide), Langmuir, 2007, pp. 9429-9434, vol. 23.

Oh et al., Secondary Structure Effect of Polypeptide on Reverse Thermal Gelation and Degradation of L/DL-Poly (alanine)-Poloxamer-L/DL-Poly(alanine) Copolymers, Macormolecules, 2008, pp. 8204-8209, vol. 41.

Park et al., PDMS-based polyurethanes with MPEG grafts: Mechanical properties, bacterial repellency, and release behavior of rifampicin, J. Biomater. Sci. Polymer Edn., 2001, pp. 629-645, vol. 12, No. 6.

Park et al., Injectable biodegradable hydrogel composites for rabbit marrow mesenchymal stem cell and growth factor delivery for cartilage tissue engineering, Biomaterials, 2007, pp. 3217-3227, vol. 28.

Rafat et al., PEG-stabilized carbodiimide crosslinked collagen-chitosan hydrogels for corneal tissue engineering, Biomaterials, 2008, pp. 3960-3972, vol. 29.

Rickerby et al., A biomedical library of serinol-derived polyesters, Journal of Controlled Release, 2005, pp. 21-34, vol. 101.

Rockwood et al., Characterization of biodegradable polyurethane microfibers for tissue engineering, J. Biomater. Sci. Polymer Edn., 2007, pp. 743-758, vol. 18, No. 6.

Sahoo et al., Hydrolytically Degradable Hyaluronic Acid Hydrogels with Controlled Temporal Structures, Biomacromolecules, 2008, pp. 1088-1092, vol. 9.

Santiago et al., Peptide-surface modification of poly(caprolactone) with laminin-derived sequences for adipose-derived stem cell applications, Biomaterials, 2006, pp. 2962-2969, vol. 27.

Sarkar et al., Synthesis and characterization of L-tyrosine based polyurethanes for biomaterial applications, Journal of Biomedical Materials Research Part A, 2008, pp. 263-271.

Sarkar et al., Oxidative and enzymatic degradations of L-tyrosine based polyurethanes, Polymer Degradation and Stability, 2007, pp. 1994-2004, vol. 92.

Schubert et al., Oxidative biodegradation mechanisms of biaxially strained poly(etherurethane urea) elastomers, Journal of Biomedical Materials Research, 1995, pp. 337-347, vol. 29.

(56) References Cited

OTHER PUBLICATIONS

Schubert et al., Role of oxygen in biodegradation of poly(etherurethane urea) elastomers, Journal of Biomedical Materials Research, 1997, pp. 519-530, vol. 34.

Silva et al., Selective Differentiation of Neural Progenitor Cells by High-Epitope Density Nanofibers, Science, Feb. 27, 2004, pp. 1352-1355, vol. 303.

Smith et al., Uptake of drugs by catheters: the influence of the drug molecule on sorption by polyurethane catheters, Biomaterials, 1996, pp. 1469-1472, vol. 17, No. 15.

Sundback et al., Biocompatibility analysis of poly(glycerol sebacate) as a nerve guide material, Biomaterials, 2005, pgs. 5454-5464, vol. 26.

Taguchi et al., Encapsulation of chondrocytes in injectable alkali-treated collagen gels prepared using poly(ethylene glycol)-based 4-armed star polymer, Biomaterials, 2005, pp. 1247-1252, vol. 26.

Tang et al., Enzyme-induced biodegradation of polycarbonate polyurethanes: Dependence on hard-segment concentration, Wiley InterScience, 2001, pp. 516-528.

Tang et al.Enzyme induced biodegradation of polycarbonate-polyurethanes: dose dependence effect of cholesterol esterase, Biomaterials, 2003, pp. 2003-2011, vol. 24.

Tang et al., Biodegradable and biocompatible thermosensitive polymer based injectable implant for controlled release of protein, International Journal of Pharmaceutics, 2009, pp. 34-43, vol. 365.

Tomlinson et al., Pendent Chain Functionalized Polyacetals That Display pH-Dependent Degradation: A Platform for the Development of Novel Polymer Therapeutics, Macromolecules, 2002, pp. 473-480, vol. 35.

Tysseling-Mattiace et al., Self-Assembling Nanofibers Inhibit Glial Scar Formation and Promote Axon Elongation after Spinal Cord Injury, The Journal of Neuroscience, Apr. 2, 2008. pp. 3814-3823, vol. 28, No. 14.

Woodhouse et al., Investigation of recombinant human elastin polypeptides as non-thrombogenic coatings, Biomaterials, 2004, pp. 4543-4553, vol. 25.

Yao et al., The effect of laminin peptide gradient in enzymatically cross-linked collagen scaffolds on neurite growth, Journal of Biomedical Materials Research Part A, pp. 484-492.

Yeo et al., Photocrosslinkable Hydrogel for Myocyte Cell Culture and Injection, Wiley InterScience, 2006, pp. 312-322.

Yeom et al., Effect of Cross-Linking Reagents for Hyaluronic Acid Hydrogel Dermal Fillers on Tissue Augmentation and Regeneration, Bioconjugate Chem., 2010, pp. 240-247, vol. 21.

Yu et al., Peptide surface modification of methylacrylamide chitosan for neural tissue engineering applications, Wiley InterScience, 2007, pp. 243-255.

Zdrahala et al., Biomedical Applications of Polyurethanes: A Review of Past Promises, Present Realities, and a Vibrant Future, Journal of Biomaterials Applications, Jul. 1 1999, pp. 67-90, vol. 14.

Zhang et al., Loading dependent swelling and release properties of novel, biodegradable, elastic, and environmental stimuli-sensitive polyurethanes, Journal of Controlled Release, 2008, pp. 128-136, vol. 131.

Zheng Shu et al., In situ crosslinkable hyaluronan hydrogels for tissue engineering, Biomaterials, 2004, pp. 1339-1348, vol. 25.

\* cited by examiner

SEQUENCE LISTING

```
<160> NUMBER OF SEQ ID NOS: 21

<210> SEQ ID NO 1
<211> LENGTH: 5
<212> TYPE: PRT
<213> ORGANISM: Homo sapiens

<400> SEQUENCE: 1

Ile Lys Leu Leu Ile
1               5

<210> SEQ ID NO 2
<211> LENGTH: 4
<212> TYPE: PRT
<213> ORGANISM: Homo sapiens

<400> SEQUENCE: 2

Arg Glu Asp Val
1

<210> SEQ ID NO 3
<211> LENGTH: 5
<212> TYPE: PRT
```

```
<213> ORGANISM: Homo sapiens

<400> SEQUENCE: 3

Arg Gly Asp Ser Pro
1               5

<210> SEQ ID NO 4
<211> LENGTH: 4
<212> TYPE: PRT
<213> ORGANISM: Homo sapiens

<400> SEQUENCE: 4

Arg Gly Asp Val
1

<210> SEQ ID NO 5
<211> LENGTH: 5
<212> TYPE: PRT
<213> ORGANISM: Homo sapiens

<400> SEQUENCE: 5

Leu Arg Gly Asp Asn
1               5

<210> SEQ ID NO 6
<211> LENGTH: 4
<212> TYPE: PRT
<213> ORGANISM: Homo sapiens

<400> SEQUENCE: 6

Arg Gly Asp Thr
1

<210> SEQ ID NO 7
<211> LENGTH: 5
<212> TYPE: PRT
<213> ORGANISM: Homo sapiens

<400> SEQUENCE: 7

Tyr Ile Gly Ser Arg
1               5

<210> SEQ ID NO 8
<211> LENGTH: 6
<212> TYPE: PRT
<213> ORGANISM: Homo sapiens

<400> SEQUENCE: 8

Thr Thr Ser Trp Ser Gln
1               5

<210> SEQ ID NO 9
<211> LENGTH: 8
<212> TYPE: PRT
<213> ORGANISM: Homo sapiens

<400> SEQUENCE: 9

Ala Glu Ile Asp Gly Ile Glu Leu
1               5

<210> SEQ ID NO 10
<211> LENGTH: 6
<212> TYPE: PRT
<213> ORGANISM: Homo sapiens
```

```
<400> SEQUENCE: 10

Trp Tyr Arg Gly Arg Leu
1               5

<210> SEQ ID NO 11
<211> LENGTH: 7
<212> TYPE: PRT
<213> ORGANISM: Homo sapiens

<400> SEQUENCE: 11

Ser Ile Lys Val Ala Val Ser
1               5

<210> SEQ ID NO 12
<211> LENGTH: 5
<212> TYPE: PRT
<213> ORGANISM: Homo sapiens

<400> SEQUENCE: 12

Pro Asp Ser Gly Arg
1               5

<210> SEQ ID NO 13
<211> LENGTH: 10
<212> TYPE: PRT
<213> ORGANISM: Homo sapiens

<400> SEQUENCE: 13

Arg Asn Ile Ala Glu Ile Ile Lys Asp Ile
1               5                   10

<210> SEQ ID NO 14
<211> LENGTH: 4
<212> TYPE: PRT
<213> ORGANISM: Homo sapiens

<400> SEQUENCE: 14

Asp Gly Glu Ala
1

<210> SEQ ID NO 15
<211> LENGTH: 4
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Val Thr Xaa Gly
1

<210> SEQ ID NO 16
<211> LENGTH: 6
<212> TYPE: PRT
<213> ORGANISM: Homo sapiens

<400> SEQUENCE: 16

Pro Arg Arg Ala Arg Val
1               5

<210> SEQ ID NO 17
<211> LENGTH: 19
<212> TYPE: PRT
```

```
<213> ORGANISM: Homo sapiens

<400> SEQUENCE: 17

Tyr Glu Lys Pro Gly Ser Pro Pro Arg Glu Val Val Pro Arg Pro Arg
1               5                   10                  15

Pro Gly Val

<210> SEQ ID NO 18
<211> LENGTH: 28
<212> TYPE: PRT
<213> ORGANISM: Homo sapiens

<400> SEQUENCE: 18

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 19
<211> LENGTH: 17
<212> TYPE: PRT
<213> ORGANISM: Homo sapiens

<400> SEQUENCE: 19

Arg Ile Gln Asn Leu Leu Lys Ile Thr Asn Leu Arg Ile Lys Phe Val
1               5                   10                  15

Lys

<210> SEQ ID NO 20
<211> LENGTH: 5
<212> TYPE: PRT
<213> ORGANISM: Homo sapiens

<400> SEQUENCE: 20

Ile Lys Val Ala Val
1               5

<210> SEQ ID NO 21
<211> LENGTH: 6
<212> TYPE: PRT
<213> ORGANISM: Homo sapiens

<400> SEQUENCE: 21

Ile Lys Val Ala Val Ser
1               5
```

REVERSE THERMAL GELS AND USES THEREFOR

CROSS REFERENCE TO RELATED APPLICATIONS

This application is a National Stage of International Patent Application No. PCT/US2011/027233, filed Mar. 4, 2011, which claims the benefit under 35 U.S.C. §119(e) of U.S. Provisional Application Nos. 61/310,874, filed Mar. 5, 2010, 61/389,491, filed Oct. 4, 2010, and 61/426,514, filed Dec. 23, 2010, each of which is incorporated herein by reference in its entirety.

STATEMENT REGARDING FEDERAL FUNDING

This invention was made with government support under the National Institutes of Health Grant No. EB008565. The government has certain rights in this invention.

The Sequence Listing associated with this application is filed in electronic format via EFS-Web and is hereby incorporated by reference into the specification in its entirety. The name of the text file containing the Sequence Listing is 6527_122495_ST25.txt. The size of the text file is 3,533 Bytes, and the text file was created on Aug. 24, 2012.

Provided herein are polymer compositions, methods of making polymer compositions, therapeutic products and methods of treating ocular diseases.

New and useful polymer compositions are desirable in the field or treatment of diseases and conditions, and also for the repair of tissue damage or insufficiencies (e.g., congenital), generally in the fields of drug delivery and regenerative medicine.

For example, human eyes are often exposed to various risks of ocular diseases. They can be an age-related such as macular degeneration; virulent inflammations by foreign bodies such as endophthalmitis; and systemic side effects such as diabetic retinopathy, macular edema, and retinal vein occlusion. Delivery of therapeutic agents for ocular treatments can usually be limited by insufficient ocular uptake and side effects. The most prescribed conventional ocular dosage forms are eye drops, eye ointments and suspensions. They have major disadvantages such as poor bioavailability due to rapid pre-corneal elimination, normal tears turnover and conjunctiva absorption, frequent instillation of concentrated medication, side effects due to systemic absorption of drugs. Intravitreal drug injections are the most effective way to maximize drug concentrations in the eye and reduce the loss whereas limiting systemic exposure. However, the effective management of chronic ocular conditions requires long-term frequent local administrations with over- and underdoses. Those repeated intravitreal injections are not only invasive and inconvenient for patients, but they may also greatly increase the risk of complications such as intraocular pressure elevation, cataracts, and retinal detachment.

In another example, the failure to recover the functions of damaged nerves may lead to severe conditions such as the malfunction of muscle and sensation. Although many studies on biomaterials for nerve regeneration have been reported, relatively little attention has been paid to the application of reverse thermal gelling copolymers that are gelled when temperature is above a threshold, especially those that carry functional groups. Injectable reverse thermal gelling biomaterials have recently become highly desirable due to their unique advantages, including easy use and the minimally invasive procedures for the site specific introduction into the body relative to traditional surgical techniques. Moreover, when the final shape of the material is defined by the local in vivo environment, such in situ-forming thermal gels are ideal. Most of the early applications are based on Poloxamers for delivery of protein/peptide drug, such as insulin, epidermal growth factor, bone morphogenic protein, fibroblastic growth factor, and endothelial cell growth factor with sustained release kinetic over several hours. However, they have been proven to be toxic showing that rats receiving 7.5 wt % of Poloxamers in their diet exhibited a decrease in growth rate.

SUMMARY

A novel copolymer composition that transitions from a copolymer solution below a phase transition temperature to a gel above the phase transition temperature. As a non-limiting, but preferred example, the composition is a liquid at room temperature and a gel at body temperature (e.g. 35° C.-40° C.), facilitating handling and delivery to a patient in a clinical setting. In such a case, the phase transition temperature range is about 25° C. to 40° C. It should be understood that phase transition in these systems are dependent on other factors such as solution concentration even for the same material composition. Phase transition that starts at temperatures above 35° C. are useful in some instances, but given that phase transition is generally over a range of a few degrees, a composition having a phase transition temperature above 35° C. may not completely gel at body temperatures. Phase transition temperatures below 25° C. also are useful in some circumstances, but those compositions may require refrigeration and cooling during transfer to prevent the composition from gelling during delivery and therefore are less practically useful than a composition with a phase transition temperature of from 28° C. to 30° C.

The reverse thermal gel has many uses, including as a drug delivery composition or dosage form. Active agents (e.g., drugs) or biologically functional groups (e.g., ECM epitope peptides and immune evasion peptides), can be attached to, bound to or mixed into the copolymer composition, and the composition can be delivered to a patient as a liquid at a temperature below the phase transition temperature of the composition. In certain embodiments, the active agents are one or more of an antibiotic, an anti-inflammatory agent, an antiangiogenic agent, a hormone, a cytokine, a chemokine, and a growth factor. When placed in a patient, the temperature of the composition is raised, thereby forming a hydrogel. The copolymers described herein are biodegradable and erode within the patient, slowly releasing the active agent within the structure. According to one non-limiting embodiment, the active agent is the antiangiogenic agent, bevacizumab (AVASTIN). According to another the active agent is MACUGEN pegaptanib sodium (MACUGEN). Or the active agent can be Ranibizumab (Lucentis). As shown herein, a polymer composition (PEG-Poly(serinol urethane)-PEG) comprising bevacizumab can provide excellent long-term release profiles for vitreal injection to treatment of macular degeneration. Other active agents, such as antibiotics or anti-inflammatory compositions can likewise be delivered to the eye.

Use of the compositions described herein is not limited to intra-ocular drug delivery. The compositions described herein can be used as cell growth scaffolds in vitro or in vivo. The compositions can be administered to a patient either topically, or internally. For example, an open wound can be flushed with the composition and compression applied such that the gel warms and seals off the wound. The composition can also be administered internally, for instance by any parenteral route, such as by injection by a syringe and needle, catheter, cannula or trochar. The formation of a hydrogel within a patient is expected to be able to stabilize internal damage and bleeding. As above, active agents, including cytokines, chemoattractants, growth factors, epitopes, coagulating agents, antibiotics and anti-inflammatory agents may be incorporated into the composition to facilitate in the composition serving a desired purpose. As illustrated below, the composition also show promise as a nerve growth scaffold.

Methods of making the composition also are described below. Methods of using the composition, for delivery of an active agent, as a biological scaffold (e.g., cell growth scaffold), and as a wound treatment are provided, as described below.

DETAILED DESCRIPTION

Figure 1:
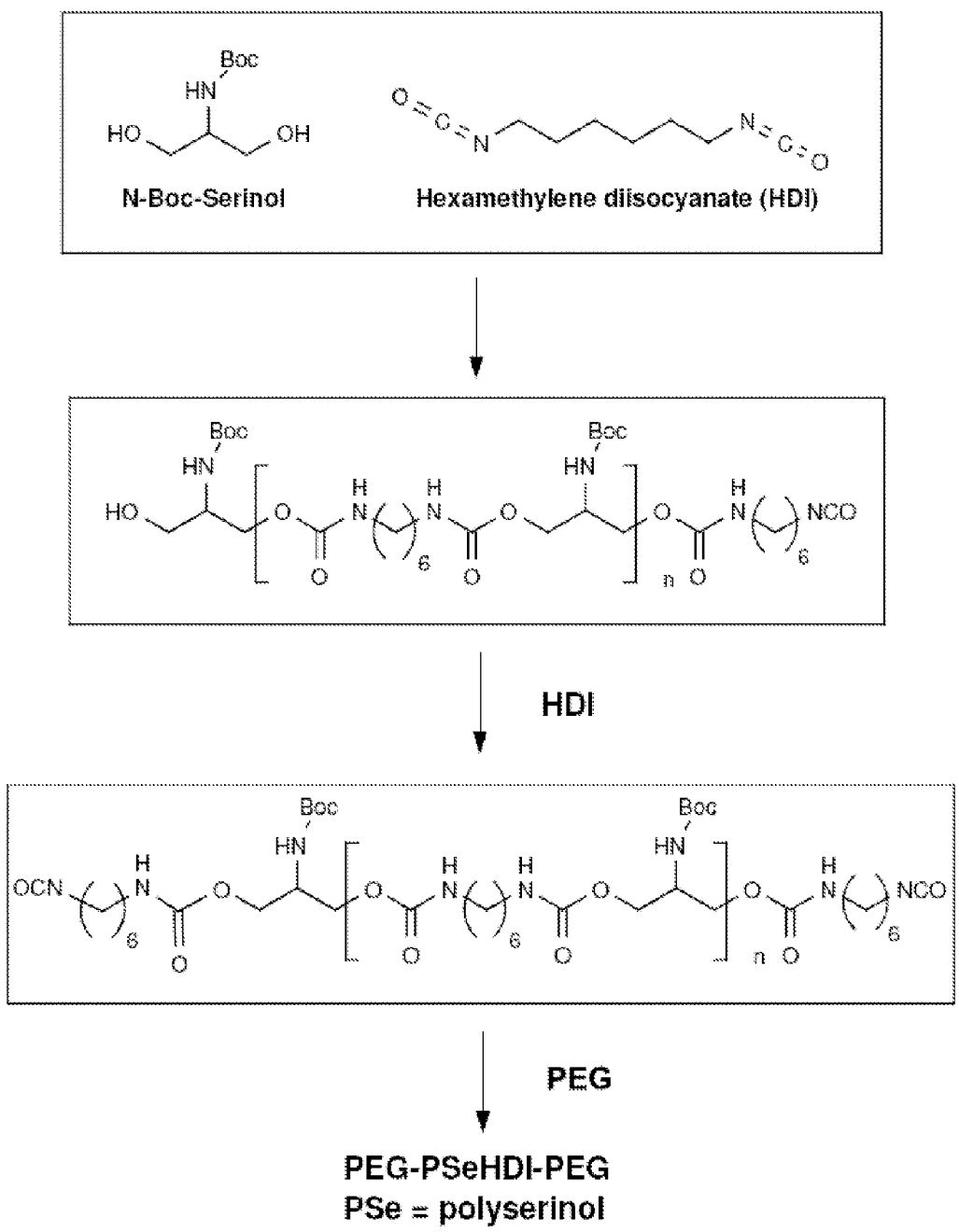
FIGS. 1 and 2 illustrate the synthesis of PEG-polyurethane (PU)-PEG and PEG-poly(ester urethane) (PEU)-PEG, respectively.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

All ranges or numerical values stated herein, whether or not preceded by the term "about" unless stated otherwise are considered to be preceded by the term "about" to account for variations in precision of measurement and functionally equivalent ranges.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

The term "alkyl" refers to both branched and straight-chain saturated aliphatic hydrocarbon groups. These groups can have a stated number of carbon atoms, expressed as $C_{x-y}$, where x and y typically are integers. For example, $C_{5-10}$, includes $C_5$; $C_6$, $C_7$, $C_8$, $C_9$, and $C_{10}$. Alkyl groups include, without limitation: methyl, ethyl, propyl, isopropyl, n-, s- and t-butyl, n- and s-pentyl, hexyl, heptyl, octyl, etc. Alkenes comprise one or more double bonds and alkynes comprise one or more triple bonds. These groups include groups that have two or more points of attachment (e.g., alkylene). Cycloalkyl groups are saturated ring groups, such as cyclopropyl, cyclobutyl, or cyclopentyl. Aromatic groups include one or more benzene rings. As used herein, "halo" or "halogen" refers to fluoro, chloro, bromo, and iodo. An amine is a group having the structure —N(R1)(R2). Where R1 and R2 are H, the group is amino.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone or are removed in the polymerization process. A polymer is said to comprise a specific type of linkage if that linkage is present in the polymer.

The polymers described herein are said to be bioerodible or biodegradable. By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months. Non-limiting examples of such chemical reactions include acid/base reactions, hydrolysis reactions, and enzymatic cleavage. The polymers described herein contain labile ester linkages. The polymer or polymers may be selected so that it degrades over a time period. Non-limiting examples of useful in situ degradation rates include between 12 hours and 5 years, and increments of hours, days, weeks, months or years therebetween. For example, in the context of an drug product to be injected via the intravitreal route, the polymer may preferably degrade over 1, 2, 3, 4, 5, 6, 7, 8, 9, 10, 11, or 12 months, or longer.

Provided is a reverse thermal gel composition comprising a triblock copolymer having the structure B-A-B in which A is one of a polyurethane or poly(ester urethane) group that comprises one or more pendant active groups, blocked active groups or active agents and B is a hydrophilic block that can be PEG of various sizes, hyaluronan of various sizes, poly (vinyl alcohol) or oligo(vinyl alcohol), polycarbohydrage, etc. Examples of poly(ethylene glycol) average molecular weights include 350, 550, 750, 1000, and 1900 Da. The composition is in solution at a lower temperature, e.g., at room temperature and transitions to a gel as the temperature is raised, to form a complete gel at a higher temperature, e.g., physiological (body) temperature (e.g., 35° C.-40° C.). The transition temperature also may be referred to as the Lower Critical Solution Temperature, or LCST) is preferably 30° C. or less or 25° C.-30° C. As an example, the transition point is above room temperature (RT, for example 25° C.) and physiological temperature (typically 37° C. but there can be individual differences). As a further example, the composition begins transformation as the temperature rises from 25° C. and forms a gel around 33-35° C. and still remains gel at 37° C. The triblock copolymer may be converted to a pharmaceutically acceptable salt. In one embodiment, A is a copolymer of a diol (a hydrocarbon comprising aliphatic or aromatic groups and which may be saturated or unsaturated) and a diisocyanate. The diol may be amino-substituted or N-substituted serinol, such as N-boc serinol, in which the N is substituted with one of a hydrogen, a protective group (a removable group that prevents the amine or other desirable moiety from reacting during synthesis of the triblock copolymer), or an active agent. In another embodiment, the N of the N-substituted serinol is —NHR in which R is a protective group, such as carbobenzyloxy; p-methoxybenzyl carbonyl; tert-butyloxycarbonyl; 9-fluorenylmethyloxycarbonyl; benzyl; p-methoxybenzyl; 3,4-dimethoxybenzyl; p-methoxyphenyl; tosyl; nosyl (4-nitrobenzenesulfonyl) and 2-nitrobenzenesulfonyl.

In another embodiment, the diol comprises one or more ester groups, as when it is a reaction product of a cyclic anhydride and a diol comprising one or more pendant active groups, blocked active groups or active agents. For example, the diol in one particular embodiment is the reaction product of succinic anhydride and an N-substituted serinol in which the N is substituted with one of a hydrogen, a protective group, such as carbobenzyloxy; p-methoxybenzyl carbonyl; tert-butyloxycarbonyl; 9-fluorenylmethyloxycarbonyl; benzyl; p-methoxybenzyl; 3,4-dimethoxybenzyl; p-methoxyphenyl; tosyl; nosyl (4-nitrobenzenesulfonyl) and 2-nitrobenzenesulfonyl, or an active agent. In one embodiment, the diol comprises a pendant amino group or an amine. One example of a diisocyanate is hexamethylene diisocyanate (1,6-diisocyanatohexane).

According to one embodiment, the composition comprises a copolymer comprising the structure:

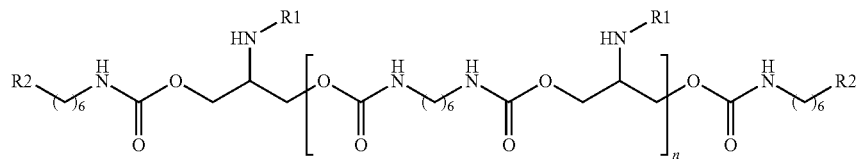

in which R1 is H or a protective group, R2 is isocyanate or —NC(O)-PEG and n is greater than 5, for example and without limitation, 8-30, 8-25 or 18-30.

According to another embodiment, the composition comprises a copolymer comprising the structure:

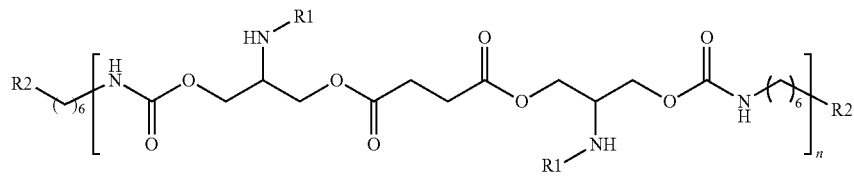

in which R1 is H or a protective group or an active agent, R2 is isocyanate or —NC(O)-PEG and n is greater than 5, for example and without limitation, 8-30, 8-25 or 18-30.

In one embodiment, the triblock copolymer has an average molecular weight of between about 3,000-50,000 Da (Daltons), for instance between 5,000 and 10,000 Da, excluding, when present, the molecular weight of the active agent. The composition may comprise an active agent complexed (non-covalently bound) to a triblock copolymer as described above. According to one non-limiting embodiment, the active agent is the antiangiogenic agent, bevacizumab (AVASTIN). According to another the active agent is MACUGEN pegaptanib sodium (MACUGEN).

Also provided is a method of delivering an active agent to a patient, comprising delivering to the patient a reverse thermal gel composition comprising an active agent and a triblock copolymer having the structure B-A-B in which A is one of a polyurethane or poly(ester urethane) group that comprises one or more pendant active groups, blocked active groups or active agents and B is a poly(ethylene glycol) and which is a gel at 37° C. and a liquid at a temperature below 30° C. In one embodiment, the active agent is an antiangiogenic agent, such as bevacizumab. The composition may be any composition described above, for example a composition comprising a triblock copolymer chosen from one of:

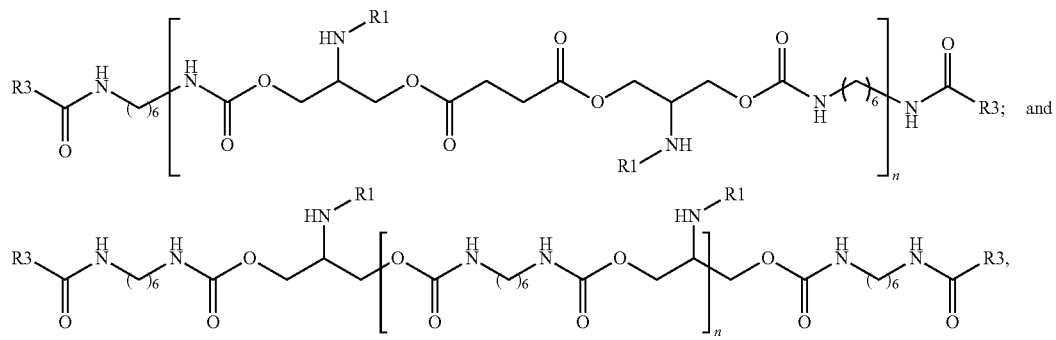

in which R1 is H and R3 is PEG, and which is complexed with an antiangiogenic agent, such as bevacizumab.

In another embodiment, a method of treating a wound or defect in a patient is provided, comprising delivering to a site in or on the patient a reverse thermal gel composition as described herein. Where the site in the patient is internal, the composition is delivered by a needle, cannula, catheter, trochar or any similar devices.

According to another embodiment, a method of making a triblock copolymer is provided. The method comprises: reacting a diol with a diisocyanate to produce a diol product; and PEGylating the diol product. In one embodiment, the idol is synthesized by reacting a diol precursor with a cyclic anhydride. An example of a diol precursor is N-serinol in which the N is substituted with a protective group, such as Boc such that the diol precursor is N-boc-serinol. In another embodiment, the cyclic anhydride is succinic anhydride. Any embodiment of these methods may further comprise complexing the triblock copolymer with an active agent. In one embodiment, the diol precursor is N-serinol, in which the N is substituted with a protective group, for instance N-boc serinol. In yet another embodiment, the diisocyanate is hexamathylene diisocyanate.

The polymer compositions may be modified to include biologically active groups or active agents either covalently bound (attached) to the polymer structure or bound to the structure non-covalently. Active agents can be admixed with the polymer composition, absorbed or adsorbed into the composition. Active agents that may be incorporated into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethisone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (.+-.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

Active agents that may be bound to the polymer composition include peptides (e.g., ECM epitopes) for functionalizing the gel with a biologically functional group. Useful peptides include or consist of the following amino acid sequences: IKLLI (SEQ ID NO: 1)(anti-apoptotic), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11), PDSGR (SEQ ID NO: 12), RNIAEIIKDI (SEQ ID NO: 13), DGEA (SEQ ID NO: 14), VTXG (SEQ ID NO: 15), PRRARV (SEQ ID NO: 16), YEKPGSPPREV-VPRPRPGV (SEQ ID NO: 17), RPSLAKKQRFRHRN-RKGYRSQRGHSRGR (SEQ ID NO: 18), RIQNLLKITNL-RIKFVK (SEQ ID NO: 19), RGD, IKVAV (SEQ ID NO: 20) and IKVAVS (SEQ ID NO: 21). In one example, these oligopeptides are linked via their amine groups to the polymeric structures described herein. In another embodiment, biomolecules are attached or bound to the polymer composition which aid in evasion of an immune response. Non-limiting examples of such peptides are: betaine, derivatives of betaine, and other zwitterionic groups including certain amino acids and their derivatives.

The active agent or any compound or composition may be bound to the polymer in any useful manner, for instance: covalently (including by coordination and by use of a suitable linkers and linking methods as are broadly known and are broadly available in the art, for example linkers and methods of use of linkers are commercially available from Thermo Fisher Scientific, Pierce Protein Research Products, Rockford, Ill., see also Thermo Scientific Pierce Crosslinking Technical Handbook, 2009 Thermo Fisher Scientific Inc.), by affinity or charge (that is, non-covalently), or by intermixing with the polymer when the composition is in solution phase. Binding of the active agent or any compound or composition by affinity or charge, e.g., by polar, hydrogen bonding, charge (ionic/electrostatic), or van der Waals interactions, may be preferred in many instances because the compound is not free to diffuse prior to or after gelation, as in the case of the active agent being intermixed with the polymer in the composition, or is not covalently modified, which can hamper efficacy of the active agent.

In one embodiment, the active agent is used for prevention or treatment of an ocular disease (disorder or condition), such as a maculopathy, a retinopathy, glaucoma, an inflammatory condition, a bacterial infection, a viral infection or a wound. The composition comprising the active agent is delivered to the eye in any useful fashion. In order to ensure consistent delivery, in one embodiment, the composition is delivered by intravitreal injection. In that case, the composition slowly breaks down in the vitreous humor and the drug is released as the composition breaks down. Suitable active agents include without limitation: antibiotics, anti-inflammatory agents, analgesics, antiangiogenic agents, and growth factors.

Non-limiting examples of antiangiogenic agents include: Macugen (pegaptanib sodium); Lucentis; Tryptophanyl-tRNA synthetase (TrpRS); AdPEDF; VEGF TRAP-EYE; AG-013958; Avastin (bevacizumab); JSM6427; TG100801; ATG3; Perceiva (originally sirolimus or rapamycin); E10030, ARC1905 and cololiximab (Ophthotech) and Endostatin. Ranibizumab is currently the standard in the United States for treatment of neovascular AMD. It binds and inhibits all isoforms of VEGF. Although effective in many cases, treatment with ranibizumab requires sustained treatment regimens and frequent intravitreal injections. VEGF Trap is a receptor decoy that targets VEGF with higher affinity than ranibizumab and other currently available anti-VEGF agents. Blocking of VEGF effects by inhibition of the tyrosine kinase cascade downstream from the VEGF receptor also shows promise, and includes such therapies as vatalanib, TG100801, pazopanib, AG013958 and AL39324. Small interfering RNA technology-based therapies have been designed to downregulate the production of VEGF (bevasiranib) or VEGF receptors (AGN211745). Other potential therapies include pigment epithelium-derived factor-based therapies, nicotinic acetylcholine receptor antagonists, integrin antagonists and sirolimus. (See, e.g., Chappelow, A V, et al. Neovascular age-related macular degeneration: potential therapies, Drugs. 2008; 68(8):1029-36 and Barakat M R, et al. VEGF inhibitors for the treatment of neovascular age-related macular degeneration, Expert Opin Investig Drugs. 2009 May; 18(5):637-46.

An anti-inflammatory agent may be administered in an amount effective to decrease ocular inflammation and pain associated with a given condition. Steroidal anti-inflammatories are useful, but not preferred because they can cause corneal thinning. Non-steroidal anti-inflammatories (NSAIDs) suitable for ocular use are preferred and include, without limitation: nepafenac (for example and without limitation, Nevenac 0.1%, nepafenac ophthalmic suspension, Alcon Laboratories, Inc.), ketorolac tromethamine (for example and without limitation, Acular LS 0.4%, ketorolac tromethamine ophthalmic suspension, Allergan, Inc.), acetaminophen and bromfenac (for example and without limitation, Xibrom 0.09%, bromfenac ophthalmic suspension, Ista Pharmaceuticals). Thus, also provided herein is a composition comprising the described block copolymer and a pharmaceutically acceptable anti-inflammatory suitable for optical use. These anti-inflammatory compounds often exhibit analgesic effects. In any case, according to the methods described herein, the binding reagent and the anti-inflammatory may be contained in the same composition, but also may be administered separately in a manner effective to treat the infection.

An antibiotic also may be administered along with the block copolymer and, optionally, the anti-inflammatory agent may also be co-administered with the antibiotic, all in an amount effective to treat and/or prevent infection and/or its symptoms. Non-limiting examples of suitable antibiotics include: ciprofloxacin, norfloxacin, afloxacin, levofloxacin, gentamicin, tobramycin, neomycin, erythromycin, trimethoprim sulphate, and polymixin B. Antiviral compounds also may be administered in this manner, such as ganciclovir or fomivirsen.

In any case, as used herein, any active agent used for prevention or treatment of a condition, such as, for example, a maculopathy, such as age-related macular degeneration, diabetic retinopathy, or ocular infection, is administered in an amount effective to treat or prevent that condition, namely in an amount and in a dosage regimen effective to prevent or reduce the duration and/or severity of the condition. As an example, between 1 and 500 mg, for example from 1.25 and 60 mg of AVASTIN (bevacizumab) can be administered in one intravitreal injection when mixed with the block copolymer. The actual amount of active agent present in the composition will depend on the degradation rate of the copolymer and dissociation rate of the agent from the composition. The ordinary intraocular injection dose for AVASTIN is 1.25-2.5 mg per month. If the gel degrades over 6 months, the amount in each "gel" dose would contain 7.5-15 mg AVASTIN, 15-30 mg if the composition degrades over a year. Different concentrations and specific activities of active agents will achieve similar results. The composition (drug product) may be administered once or more than once, depending on the duration of the erosion of the block copolymer. For example, the composition can be administered monthly, bimonthly, quarterly or yearly. The amount (e.g., number of drops of drug product) of the drug product administered to the patient, also may vary though the amount administered should not be either harmful to the patient or interfere other than insubstantially with functioning, such as vision.

Non-limiting examples of growth factors suitable for ocular use include: non-mitogenic human acidic fibroblast growth factor (nm-haFGF), neurotrophin nerve growth factor (NGF), epidermal growth factors (EGF), brain-derived neurotrophic factor (BDNF), glial cell line-derived neurotrophic factor (GDNF), neurotrophin-3 and eye-derived growth factor(s) (EDGF).

In one embodiment, a combined dosage form is provided comprising two or more of an anti-angiogenic agent, an anti-inflammatory agent, an antibiotic agent and a growth factor. For example, either an antibiotic or antiviral agent may be co-administered with an anti-inflammatory agent.

In any use for the prevention and/or treatment of any condition in a patient, a person of ordinary skill in the pharmaceutical and medical arts will appreciate that it will be a matter of simple design choice and optimization to identify a suitable dosage regimen for treatment of any given condition using the delivery systems/compositions described herein. As such, the composition may comprise a carrier, such as an opthamologically-acceptable carrier, which comprises acceptable excipients, such as, without limitation, one or more suitable: vehicle(s), solvent(s), diluent(s), pH modifier(s), buffer(s), salt(s), colorant(s), rheology modifier(s), lubricant(s), antifoaming agent(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water, as are broadly known in the pharmaceutical arts.

The compositions described herein may find use as cell growth scaffolds. Cells may be microintegrated within a cell growth matrix using a variety of methods. In likely the simplest embodiment to implement, the cells are mixed with the copolymer when it is a miscible liquid, below the gelation temperature. The following are examples of methods used to incorporate cells into traditional cell scaffolds that are gelled or solid at the time of cell incorporation. They may be useful in case where a cell type would need to be preconditioned to the matrix prior to implantation. In the context of the present disclosure, the gel may be warmed until it gels and then cells are incorporated, for example, as follows. In each case, the gel would need to be kept above the gelation temperature throughout. However, reduction of the temperature until the gel/cell mixture is a miscible liquid may be desirable for the purpose of either facilitating delivery to a patient through a needle or catheter, or for isolating cells, in that the solution can be centrifuged to pellet the cells.

In one example, a gel is submersed in an appropriate growth medium for the cells to be incorporated, and then directly exposed to the cells. The cells are allowed to proliferate on the surface and interstices of the matrix. The matrix is then removed from the growth medium, washed if necessary, and implanted. Cells of interest also can be dissolved into an appropriate solution (e.g., a growth medium or buffer) and then sprayed onto a growth matrix. This method is particularly suitable when a highly cellularized tissue engineered construct is desired. In one embodiment, pressure spraying (i.e., spraying cells from a nozzle under pressure) is used to deposit the cells. In another, the cells are electrosprayed onto the non-woven mesh during electrodeposition. Electrospraying involves subjecting a cell-containing solution with an appropriate viscosity and concentration to an electric field sufficient to produce a spray of small charged droplets of solution that contain cells.

Many cell types require a support cell population or matrix in order to, for example, survive, grow, propagate or differentiate. As indicated above, cells can be mixed with the composition at a temperature below the gelation temperature for the composition. Next, the temperature of the composition is raised to produce a gel containing the cells. The cells are grown at a temperature at which the composition is gelled. Lastly, the cells can be removed from the gel by first lowering the temperature of the composition to below the gelation temperature to "melt" the gel, and then the cells are washed, e.g., with medium, saline or PBS (Phosphate-Buffered Saline) to remove the polymer composition. By this method specific shapes of tissue may be generated, for instance by growing the cells in a mold, and letting the cells grow/differentiate until cell-cell interaction is achieved. Once the cells or tissue is grown, the cells or tissue can then be washed free of any remaining polymer.

The cells that may be incorporated on or into the gel includes stem cells such as adipose or neural stem cells; progenitor (precursor) cells; smooth muscle cells; skeletal myoblasts; myocardial cells; endothelial cells; endothelial progenitor cells; bone-marrow derived mesenchymal cells and genetically modified cells. In certain embodiments, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF or FGF-2), acidic fibroblast growth factor (aFGF), nerve growth factor (NGF), vascular endothelial growth factor (VEGF), hepatocyte growth factor (HGF), insulin-like growth factors (IGF), transforming growth factor-beta pleiotrophin protein, midkine protein.

In one embodiment of the methods described herein, the composition, with or without cells, growth factors, active agents, etc. is injected or deposited at the site of a wound to heal the wound. Wrapping or covering the wound, e.g., in bandages can insure that the composition remains at a temperature at which it is a gel. The composition with or without cells, growth factors, active agents, etc., can be injected or otherwise administered at any point in or on a patient. For instance a catheter, cannula, trochar, syringe, etc. can be used to deliver the composition to a desired location. In one embodiment, a method of growing nerve cells, such as a method of repairing a nerve, is provided. In one embodiment, the composition is implanted in a wound to a nerve so that nerve cells can populate the hydrogel and nerve structure and function is regenerated. For example, the composition can be implanted at a site of a spinal cord wound (see below for an example) and the nerve tissue is regenerated.

Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

As described above, the compositions described herein are useful for drug delivery, especially were systemic treatment is not necessary or dangerous. One or more therapeutic agents may be included in the compositions and the composition is delivered to a site in a patient, where the composition gels. Delivery of the composition is limited by the rate of degradation of the polymeric component of the composition. As such, the composition may be useful in treating tumors, for example, by complexing an anticancer agent with the polymeric component of the composition and delivering the composition to the site of a tumor, where it slowly releases the anticancer agent. Likewise, these compositions may find use in treating localized conditions, such as abcesses. The composition may be useful in delivering steroids at a constant rate, for example in the case of testosterone, where less than optimal injections, topical gels and patches are the norm, or contraceptives.

Example 1

This study aims to develop injectable reverse thermal gelling triblock copolymers with serinol-derived polyurethane (PU) and polyester urethane (PEU) and study its potential as nerve regenerative matrices. PUs are useful materials in biomedical fields since they have been proven to be biocompatible. (Zdrahala, R. J.; Zdrahala, I. J. *J. Biomater. Appl.* 1999, 14, 67-90). They are easily tailored by changing hard segment chemistries and concentrations leading to the intended functions. (Tang, Y. W.; Labow, R. S.; Santerre, J. P. *Journal of Biomedical Materials Research* 2001, 57, 597-611 and Tang, Y. W.; Labow, R. S.; Santerre, J. P. *J. Biomed. Mater. Res.* 2001, 56, 516-528). The applications of PUs have been extended to catheters, compliant vascular grafts, and prosthetic valve leaflets since the first introduction as materials for breast prostheses.

Thus, the incorporation of biocompatible PUs with serinol and PEG resulting in functionalized injectable reverse thermal gelling copolymers will be the breakthrough in the field of tissue engineering, especially in the nerve regeneration.
Synthesis of Thermal Gelling Copolymers In first step, two types of thermal gelling copolymers, PEG-polyurethane (PU)-PEG and PEG-poly(ester urethane) (PEU)-PEG, were designed (See FIGS. 1 and 2). PU was synthesized using N-BOC-serinol and hexamethylene diisocyanate (HDI) at 90° C. The attachment of PEG was performed by the formation of urethane bonds with HDI. PEU was synthesized in two steps. First, the esters were synthesized using N-BOC-serinol and succinic anhydride at 90° C. Then the as-synthesized esters reacted with HDI at 90° C. to make PEU followed by PEG attachment.

Figure 3A:
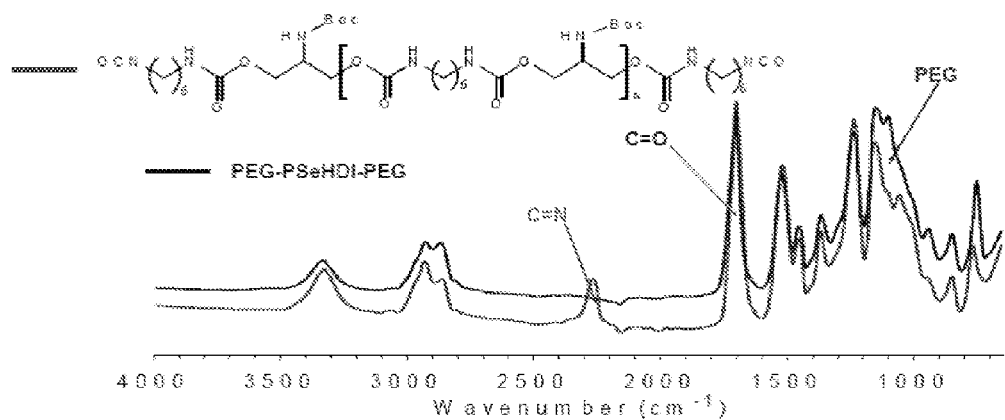
FIGS. 3A and 3B show FT-IR characterization of PEG-polyurethane (PU)-PEG and PEG-poly(ester urethane) (PEU)-PEG, respectively.
Figure 3B:
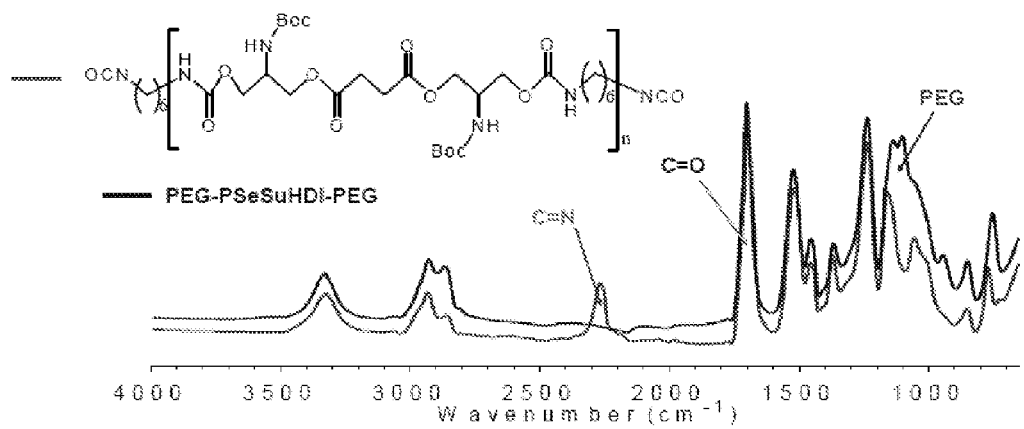

The PEG-PU-PEG was characterized by FT-IR (FIGS. 3A and 3B which showed bands of C=N by HDI and C=O by urethane bonds at 2270 and 1650-1680 cm$^{-1}$ respectively. The C=N peak disappeared after the PEG attachment whereas ether, R—O—R, signal by PEG appeared at 1000-1150 cm$^{-1}$. For the synthesis of PEG-PEU-PEG, the bands of C=N by HDI, C=O by urethane and ester bonds, and R—O—R by PEG in PEU appeared at 2270, 1600-1750, and 1000-1150 cm$^{-1}$, respectively.

Thermal Behavior of Copolymers

The phase transition from solution to gel largely depends on the balance of hydrophilic (PEG) and hydrophobic (PU, PEU) portions in copolymer structures. In addition, by modulation of the length of hydrophobic parts the gelling temperature can be adjusted. Based on these facts we developed specifically designed thermal gelling copolymers with phase transition at physiologically important temperature range of 32-37° C. The storage modus (G') of the polymer solutions in PBS solution was measured by rheometer from 20° C. to 55° C.

Figures 4A, 4B:
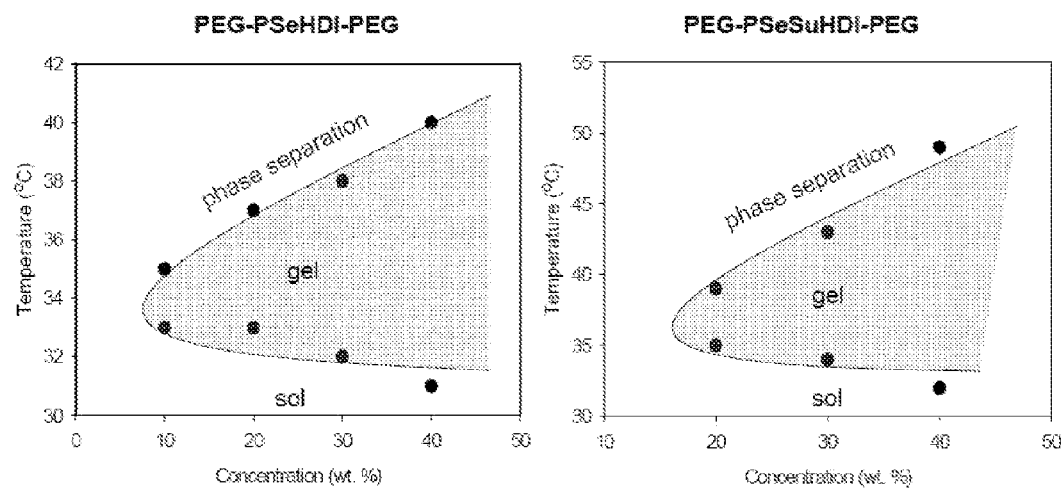
FIGS. 4A and 4B provide graphs showing thermal behavior of PEG-polyurethane (PU)-PEG and PEG-poly(ester urethane) (PEU)-PEG, respectively.

The thermal behavior showed that the aqueous polymer solution of PEG-PU-PEG prepared with 30 and 40% (wt) concentrations started phase transition from 31-32° C. and remained gel in the temperature range of 37-40° C. For the aqueous solution of PEG-PEU-PEG, they remained gel in the temperature range of 35-37° C. with all concentrations tested (FIGS. 4A and 4B). The implication of these graphs are that the compositions, with an increase in temperature will solidify, so long as the concentration of the polymer in solution is above a minimal concentration as shown in FIGS. 4A and 4B. For example, for PEG-PSeHDI-PEG, for concentrations between about 8% (wt) and 50% (wt), the composition is a solution at low temperatures, such as below about 32% (wt), and phase separation occurs at a higher temperature, such as at about 38° C. for a 30% (wt) solution of the copolymer. Thus, for typical uses in humans, a temperature range at which the composition is preferably a gel is, for example, between 32-40° C. or 32-38° C., meaning the concentration of the copolymer may be preferably between 20% (wt) to 50% (wt). For PEG-PSeSuHDI-PEG, the concentration of the copolymer may be preferably between 15% (wt) to 50% (wt).

Figure 5:
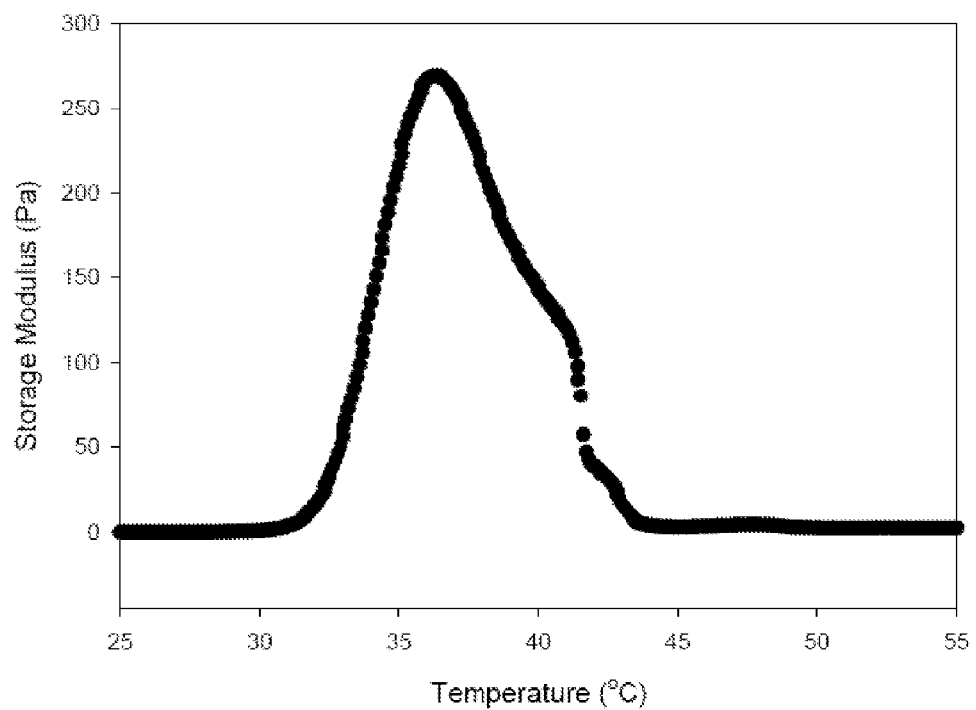
FIG. 5 shows storage modulus changes of 30% (wt) PEG-PU-PEU solution.

FIG. 5 shows storage modulus changes of 30% (wt) PEG-PU-PEU solution. No significant changes of the storage modulus (G') were observed until 31° C. indicating that it remained fluidic; a dramatic increase in the storage modulus were observed between 32-36° C. indicating the gelation, and the decrease in modulus occurred showing the phase separation.

Degradation of PEG-PU-PEG and PEG-PEU-PEG

For biodegradability, the copolymer solution was treated with both PBS solution and cholesterol esterase, and the molecular weights were measured every 7 days for 2 weeks. Each polymer was dissolved in both PBS solution and 400 U/ml of enzyme solutions with concentration of 5% (wt). 0.2 ml of fresh enzyme solution (2,000 U/ml) was added every three days to recover the enzyme activity.

The PEG-PU-PEG incubated in PBS solution did not show Mw changes whereas 3.4% decrease in Mw was observed in enzyme solution in two weeks. For the PEG-PEU-PEG, 5.2% decrease in Mw was observed even in PBS solution. Much higher decrease in Mw, 29.8%, was observed in enzyme solution. Thus both PEG-PU-PEG and PEG-PEU-PEG have been proven to be biodegradable (Table 1).

TABLE 1

| Degradation of PEG-PSeHDI-PEG and PEG-PSeSuHDI-PEG | | | | | | | | |
|---|---|---|---|---|---|---|---|---|
| | PBS | | | | E* (400 U/mg) | | | |
| | 7 days | | 14 days | | 7 days | | 14 days | |
| | Mw | DP | Mw | DP | Mw | DP | Mw | DP |
| PEG-PSeHDI-PEG Mw 6,211 DP 1.70 | 6,203 | 1.7 | 6,230 | 1.71 | 6,048 | 1.75 | 5,998 | 1.78 |
| PEG-PSeSuHDI-PEG Mw 9,824 DP 1.69 | 9,479 | 1.79 | 9,312 | 1.72 | 7.970 | 1.7 | 8,891 | 1.8 |

*E is cholesterol esterase from bovine pancreas (one unit will hydrolyze 1.0 nmol of cholesteryl oleate to cholesterol and oleic acid per minute at pH 7.0 at 37° C.)

Example 2

To overcome perceived drawbacks in current ocular drug products, we conceived therapeutic agent-conjugated reverse thermal gels which undergo temperature triggered sol-gel phase transition and form a gel at physiologically important temperature. Since the therapeutic agents conjugated reverse thermal gels can form gels by a simple injection in the vicinity of target area, loss of therapeutic agents can be minimized. We hypothesize that controlled release will sustain the vitreous concentration of the therapeutic agents in the therapeutic range longer with reduced side effects and treatment frequency (FIG. 6) achieving higher therapeutic indices. The specific aim is to control the release of therapeutic agents using a functionalized reverse thermal gel that gels upon reaching body temperature. We will control the release rate by varying the affinity between the gel and the therapeutic agents. We will design the density of the delivery system to approximately match that of the vitreous fluid.

Figure 6:
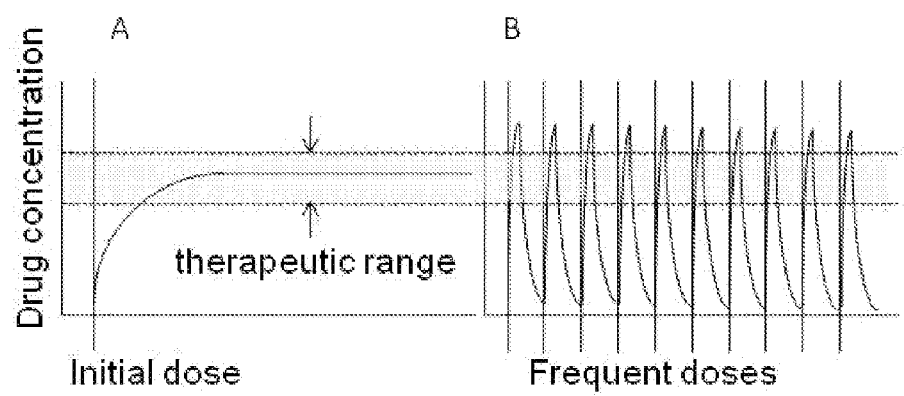
FIG. 6 shows simulated concentration profile of therapeutic agents in the vitreous fluid. (A) Proposed method that offers controlled release and a sustained concentration in the therapeutic range for a long period after one injection. (B) Current method that needs frequent injections.

FIG. 6 shows simulated concentration profile of the therapeutic agents in the vitreous fluid. (A) Proposed method that offers controlled release and a sustained concentration in the therapeutic range for a long period after one injection. (B) Current method that needs frequent injections.

Because affinity is the main factor for the conjugations, most types of therapeutic agents can be conjugated to reverse thermal gels including antiangiogenic agents for macular degeneration, antibiotics for virulent inflammation, and growth factors for ocular wound healings.

Synthesis of Reverse Thermal Gel and Conjugation to Therapeutic Agents:

We have recently designed and synthesized a biocompatible and biodegradable reverse thermal gel, PEG-Poly(serinol urethane)-PEG. This polymer gels at around 32° C. The gel will be synthesized using N-Boc-serinol, hexamethylene diisocyanate and poly(ethylene glycol) as outlined in FIG. 1. The structure of this triblock copolymer is shown below.

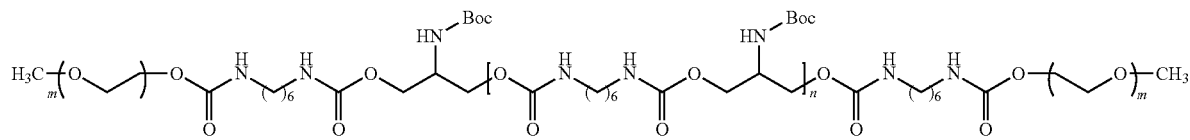

This copolymer is treated with 50% (v/v) of trifluoroacetic acid to deprotect the primary amine groups and produce ammonium groups. Therapeutic agents are mixed with 10, 15 and 20% (wt) of the ammonium-containing triblock copolymer in 0.2 ml of PBS. The negatively charged therapeutic agents, due to carboxylic acid groups, are complexed with positively-charged ammonium-containing triblock copolymer in the neutral solution by Coloumbic interaction. The affinity between therapeutic agents and the delivery polymer can lead to controlled release. The thermal behavior of therapeutic agent-complexed triblock copolymer is studied rheologically at the temperature range of 25-45° C.

Determination of Loading Efficiency:

The mixture of therapeutic agents and ammonium-containing triblock copolymer in PBS is raised to 37° C. to form a gel. 100 µl of PBS is added on top of the gel and agitated gently on an orbital shaker. The concentration of therapeutic agents in the supernatant is determined spectrophotometrically and chromatographically. The loading efficiency is calculated by the comparison of total concentration to supernatant one.

Biocompatibility and Biodegradability:

Previously we have studied in vitro biocompatibility and biodegradability of the composition Biocompatibility studied according to ISO 10993-5 guidelines revealed excellent biocompatibility. In the presence of cholesterol esterase, the molecular weight of the polymer decreased 25% in 45 days. In PBS without any enzyme, the decrease was 2.5% in 45 days. The biocompatibility and biodegradability of the compositions are investigated in vivo using New Zealand white rabbits. A 0.5 ml of 20% therapeutic agent-complexed triblock copolymer solution is injected subcutaneously into four spots in the upper and lower back on both sides of the animal. In addition, the animals will receive 1 injection of 0.05 ml of 20% therapeutic agent-complexed triblock copolymer in the anterior segment of the eye. Biocompatibility also is tested in the posterior segment of the eye if the anterior tests show promising results. Rabbits are chosen to facilitate future efficacy and safety tests including intraocular pressure tests. The animals are euthanized at 1, 3, 7, 14 and 30 days. At each time point, the cutaneous and subcutaneous tissues surrounding the injection site are harvested. The tissues are fixed, stained, and examined by standard histological analysis for any signs of acute and chronic inflammation. Control is saline solution. For biodegradability evaluation, the size and dry weight of the therapeutic agent-complexed triblock copolymer gel is measured and compared to the original size and weight.

Figure 7:
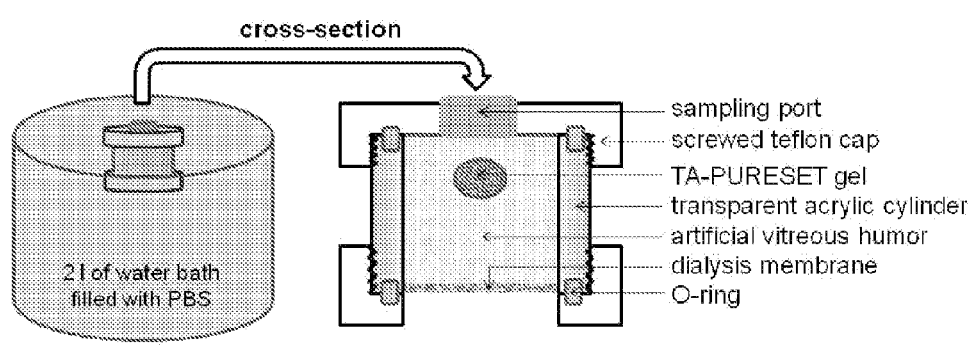
FIG. 7 shows (Left) The device for the study of the controlled release of therapeutic agents. (Right) the detailed cross-sectional view of the capsule as described in Example 2.
Figure 8:
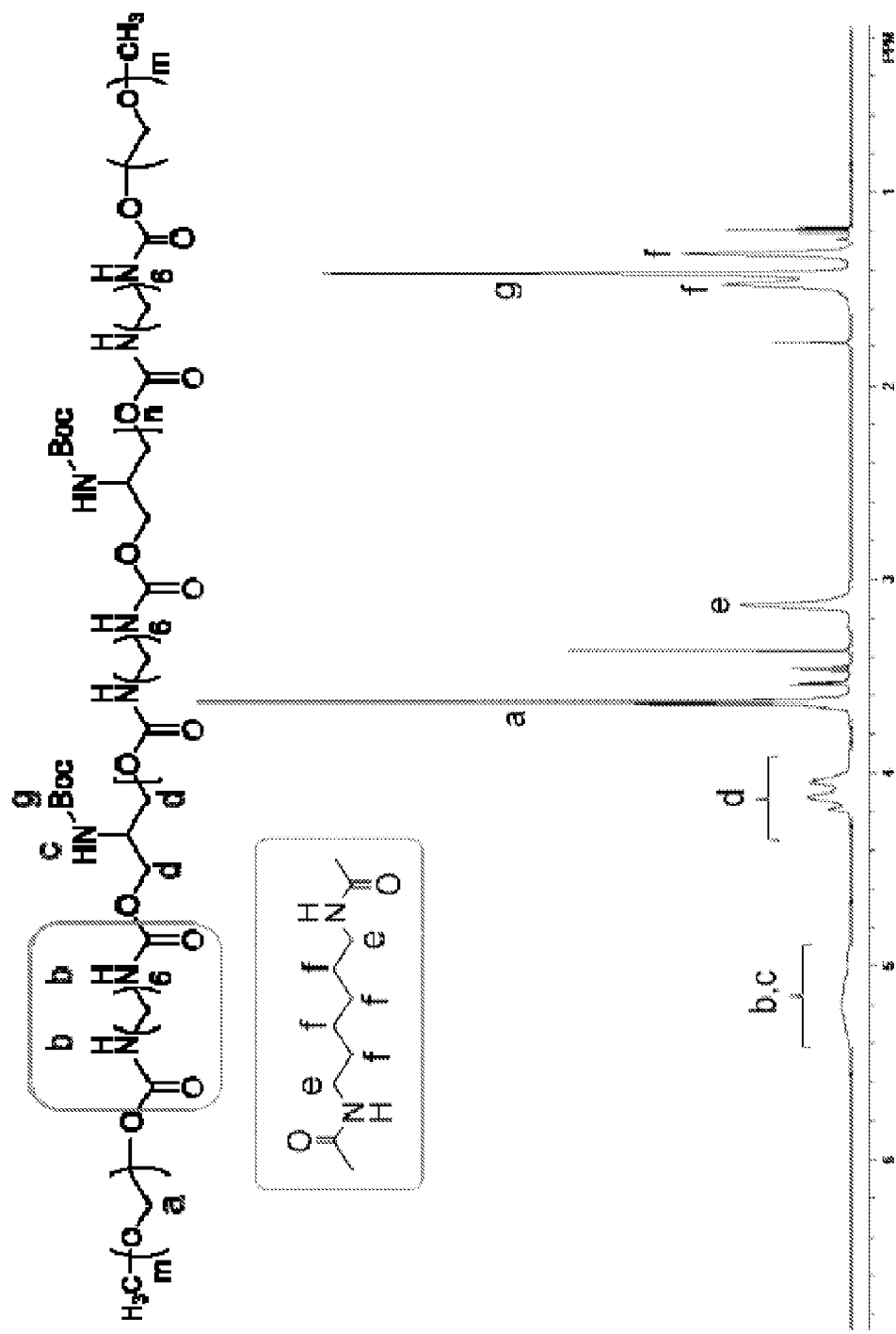
FIG. 8 provides 1H FTNMR spectra of poly (ethylene glycol)-poly(serinol hexamethylene urethane) (ESHU) in $CDCl_3$. The presence of a, e and g protons indicate the presence of PEG, polyurethane and BOC-protected amine groups in ESHU.

Control the Release of Therapeutic Agents:

The amount of therapeutic agents released is periodically measured spectrophotometrically and chromatographically in vitro using an artificial vitreous fluid. The release kinetics is measured at 37° C. in a custom made device (FIG. 7) with two compartments that mimic the eye and the body. The device will be kept under sterile conditions. The 2 liter PBS bath mimics the body. The plastic capsule mimics the eye. The dialysis membrane of the capsule allows mass transfer that simulates the mass transfer between the eye and the body. The device is filled with 7.5 ml (the volume of an adult eye is 7.2 to 7.5 ml) of artificial vitreous fluid. A 0.2 ml of the therapeutic agent-complexed triblock copolymer solution at ambient temperature is injected through the sampling port. Aliquots of the artificial vitreous fluid will be analyzed periodically between 1 and 120 days. FIG. 7. (Left) The device for the study of the controlled release of therapeutic agents. (Right) the detailed cross-sectional view of the capsule.

Example 3

Nerve Repair

When nerves are damaged slightly they can self-regenerate. However when the nerve defects or gaps are greater than 2 cm, surgical management will be a significant challenge. Many researchers have studied nerve regeneration by autologous grafts and tubular conduits, and biomaterials in which neurotransmitter, neural stem cell, and peptide are combined. These biomaterials are natural polymers such as collagen, fibrin, chitosan, and alginate and synthetic polymers. When these biomaterials are implanted into injured sites, most of them interact with invading neural cells by providing structural support, promote and eventually guide nerve growth (See, Yao, L., et al. Journal of Biomedical Materials Research Part A, J Biomed Mater Res A. 2010 February; 92(2):484-92; Gao, J., et al. *Proc. Nat'l. Acad. Sci., U.S.A., Vol.* 103, No. 45 (Nov. 7, 2006), pp. 16681-16686; and Mahoney, M J, et al. *Biomaterials* 27 (2006) 2265-2274). In one example, a composition described herein is deposited at a nerve growth site, such as a site of trauma to a nerve, so that it can serve as a nerve guide or scaffold for nerve regeneration.

Example 4

Treating Macular Degeneration with Anti-Angiogenic Reverse Thermal Gel

Age-related macular degeneration (AMD) causes yellow deposits in the macula in the dry form, or choroidal neovascularization (CNV) and profound vision loss in the wet or exudative form. As the leading cause of the blindness in individuals older than 55 years, AMD affects more than 1.75 million people in the US and the number is expected to increase to 3 million by 2020. Current treatments for wet AMD rely on photodynamic therapy and injections of anti-angiogenic agents such as Lucentis, Avastin, or Macugen. Photodynamic therapy (PDT) is based on the effect of oxygen radicals on the choroidal neovascular capillaries, where the dye is preferentially bound. However, PDT is only effective for some types of CNV and rarely improves vision. The current standard of practice is anti-angiogenic therapy based on the inhibition of vascular endothelial growth factor-A (VEGF-A) using the antibody (Avastin) or antibody fragment (Lucentis). However, because the half-life of protein-based drugs is short, the intravitreal injections are repeated frequently, sometimes monthly over several years. This creates a substantial treatment burden, requiring multiple injections and follow-up visits.

We propose to ameliorate this burden using a controlled release platform that can achieve a sustained therapeutic vitreous concentration of anti-VEGF for a long period of time. This will reduce treatment frequency, increase patient compliance and achieve a higher therapeutic index. The specific aim of this project is to control the release of anti-angiogenic agents using a transparent, biocompatible reverse thermal gel that gels upon reaching body temperature.

Synthesis of Reverse Thermal Gel

We have created a reverse thermal gel, PEG-Poly(serinol urethane)-PEG, a.k.a. ESHU (Scheme 1), using N-Boc-serinol, hexamethylene diisocyanate and poly(ethylene glycol).

Figure 9:
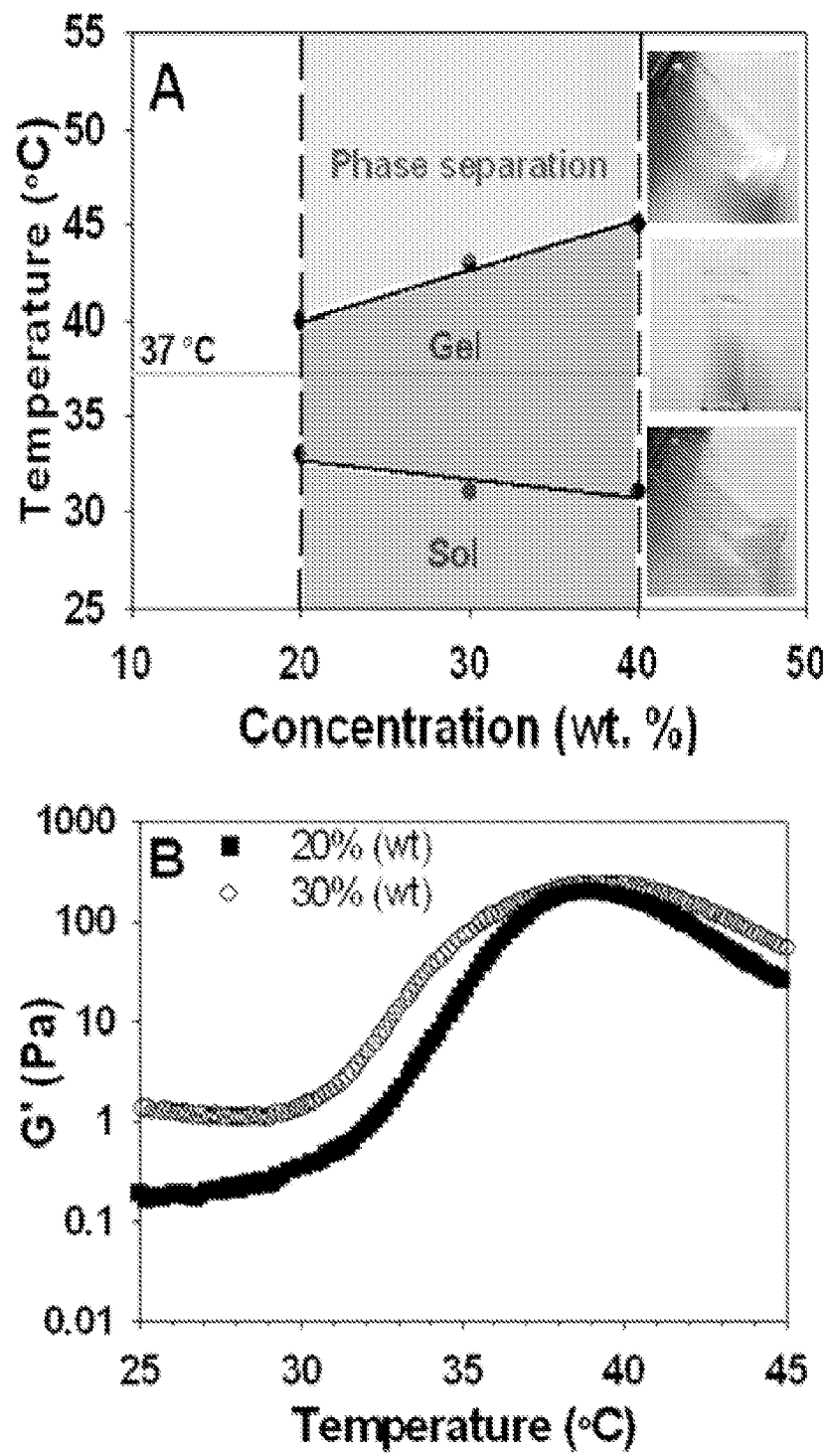
FIG. 9. Thermal behavior of ESHU. The solutions underwent temperature triggered sol (red)-gel (blue) phase transition and remained gels at 37° C. Inset shows images of the polymer solution at 3 stages corresponding to (from the bottom) sol, gel, and phase separation. (B) G' changes with temperature at 20 and 30% (wt) concentrations.

Thermal Behavior of Copolymer:

The solution of ESHU showed phase transition from solution to gel depending on temperature as well as concentrations. The solution remained gel (blue area) at body temperature in all tested concentrations (FIG. 9 (A)). The consistent storage modulus (G') of ESHU indicates that the solution remained fluidic below 30° C. The sharp increase in G' between 32-40° C. indicates gelation (FIG. 9 (B)).

Figure 10:
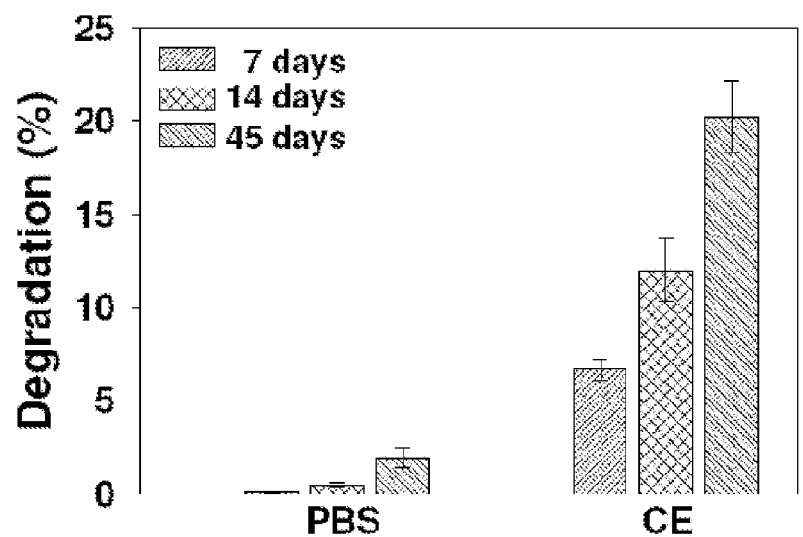
FIG. 10 is a graph showing in vitro degradation of ESHU in PBS and CE solution. The degradation of ESHU was much faster in the presence of CE. Data are presented as means±S.D (n=3).

In Vitro Biodegradability and Biocompatibility:

For biodegradability, ESHU was incubated in PBS and cholesterol esterase solution at 37° C. Degradation was determined by comparison of the molecular weights. ESHU showed a very slow degradation (2.5% in 45 days) in PBS, however, it was accelerated by cholesterol esterase (22% in 45 days) (FIG. 10).

Figure 11:
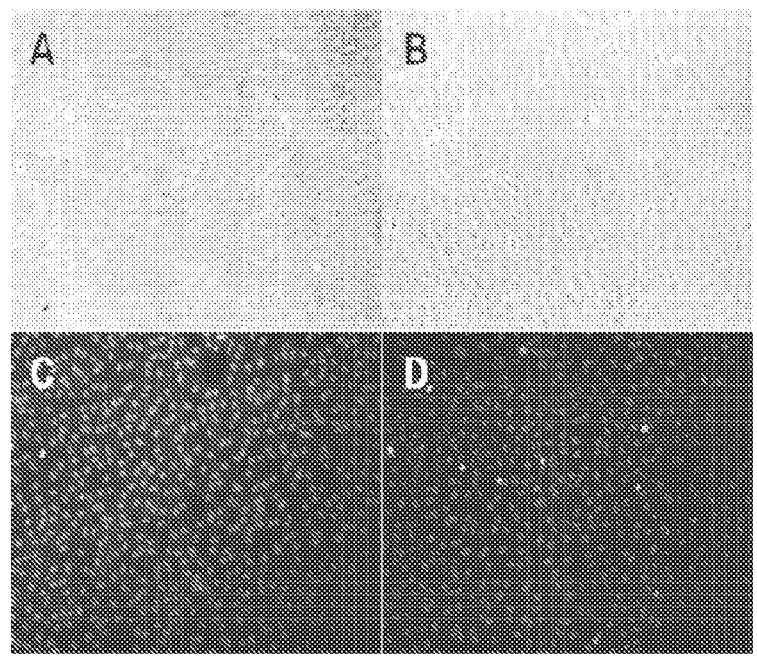
FIG. 11. In vitro cytotoxicity toward primary bovine corneal endothelium cells. Phase images (100×) of Calcein AM treated cell morphologies of (A) control and (B) ESHU. No differences were observed between control and ESHU. Fluorescence images (100×) of cells of (C) control and (D) ESHU which stained with Hoechst and propidium iodide. Most nuclei (blue dots) are intact with a few red one.

In vitro biocompatibility was examined using primary bovine corneal endothelium cells. The cells were exposed to control (serum-free DMEM) and 15% (wt) ESHU gel in DMEM for 24 hr. The cells treated with Calcein AM showed no evidence of altered cellular morphology on microscopic examination (FIGS. 11, A and B). The viability was evaluated by immunofluorescent microcropy after staining with propidium iodide and Hoechst (FIGS. 11, C and D). Cytotoxicity was calculated as propidium iodide nuclei/total nuclei. No significant damage to cultured cells by ESHU was observed compared to the control (P>0.05, two way ANOVA).

Figure 12:
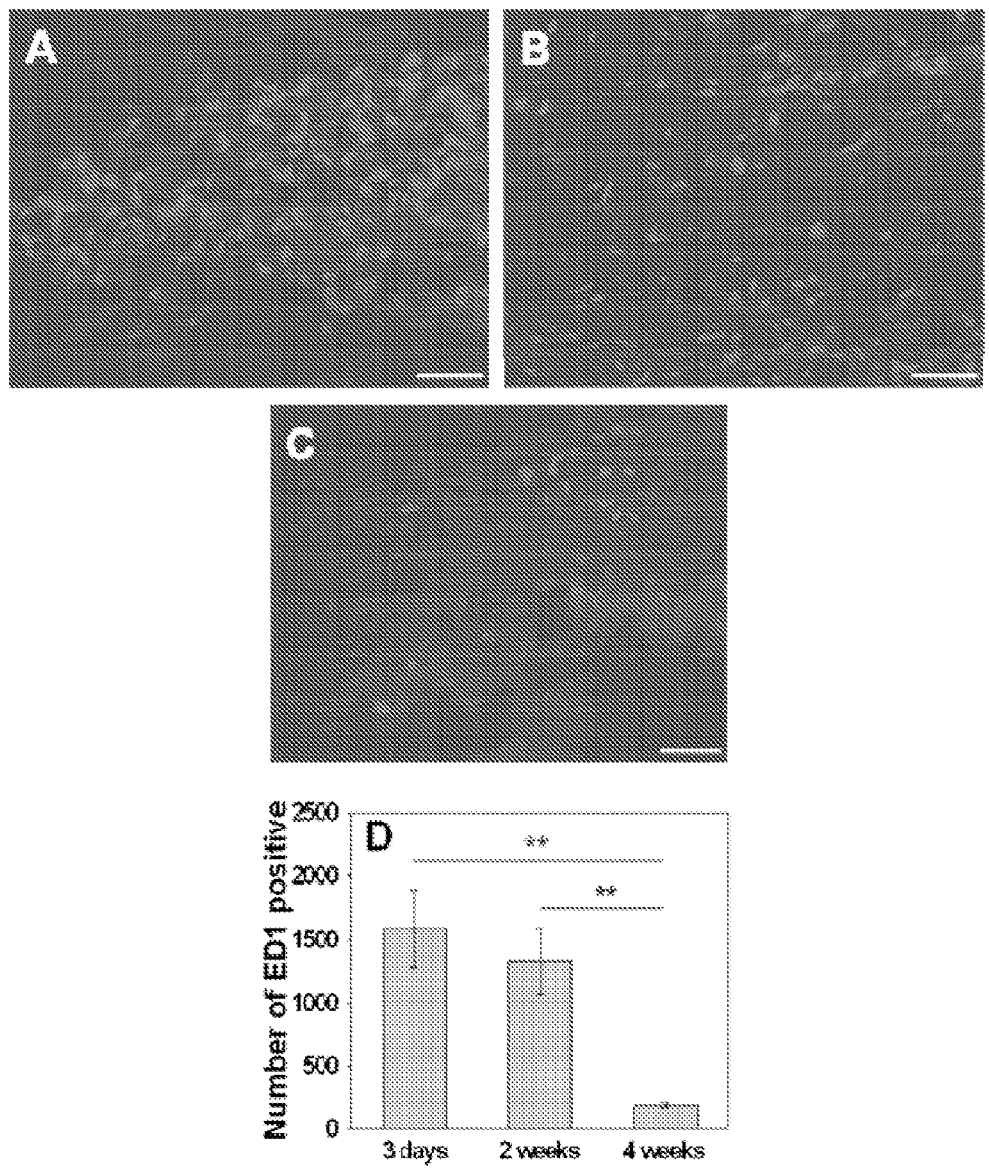
FIG. 12 provides representative fluorescent photomicrographs (200×, scale bar=60 µm) of injection sites stained for ED1+ macrophages (red in original). Tissues were harvested after: (A) 3 days; (B) 14 days, and (C) 28 days. (D) The number of ED I+ macrophages decreased with time indicating a reduction in inflammatory response. **p<0.01 (paired Student's t-test).

In Vivo Biocompatibility:

We tested in vivo biocompatibility in Sprague Dawley rats. We used near saturation concentration of ESHU (60% wt) to study the most severe host response. Subcutaneous implantation in rats revealed a well tolerated inflammatory response with moderate amount of ED-1 positive macrophages in the early stages, which largely resolved 4 weeks post-implantation (FIG. 12) indicating ESHU was biocompatible.

In Vitro Release of Avastin:

We chose Avastin (Bevacizumab) to represent antiangiogenic agents because it is the most widely prescribed AMD treatment as it is inexpensive and effective. The release tests were performed in 7.5 ml of 1% (wt) hyaluronic acid solution at 37° C. to mimic vitreous fluid and under gyroscopic shaking to mimic human eye motion. Four formulas, 15 and 20% (wt) ESHU with 0.5 and 1 mg Avastin were used. The solution gelled immediately into a sphere upon injection into the 37° C. hyaluronic acid solution and quickly sank to the bottom indicating the delivery system will be out of the optical axis of the eye. The release of active Avastin was measured by enzyme-linked immunosorbent assay (ELISA) according to manufacturer's protocol. The release is sustained and nearly Scheme 1. Chemical structure of ESHU.

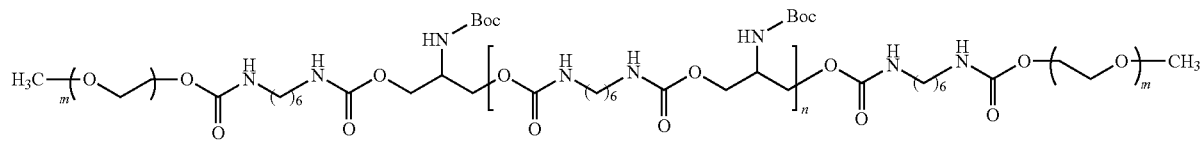

Figure 2:
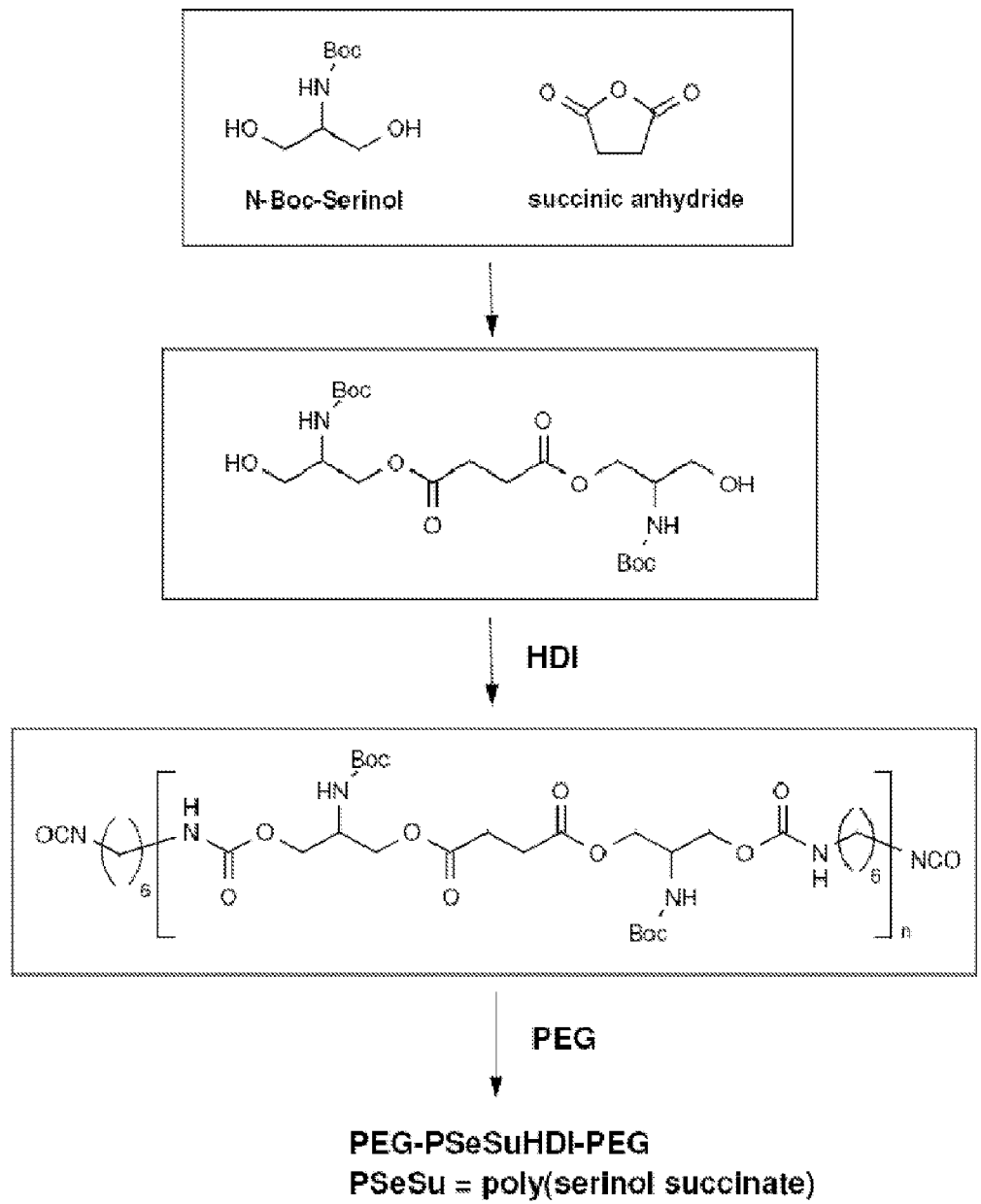
Figure 13:
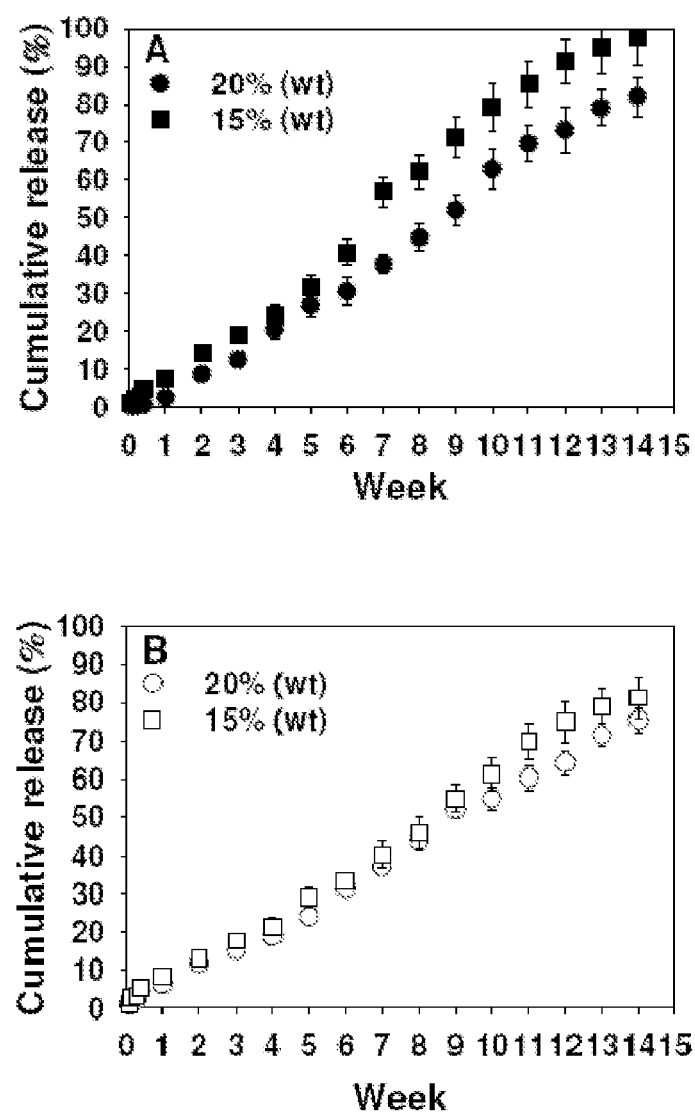
FIG. 13 provides graphs showing the release profile of Avastin from ESHU gel. (A) With 0.5 mg of Avastin, 85.1% and 96.8%, and (B) with 1 mg, 75.4% and 81.3% were released from 20% and 15% ESHU gels respectively at 14 week post injection.

We examined the chemical structures of ESHU by 1H FTNMR analysis (FIG. 1). The methylene protons in PEG (a) and N-BOC-serinol (d) were confirmed at 3.65 and 4.0-4.2 ppm, respectively. The methylene protons adjacent to nitrogen in urethane functional groups (e) were observed at 3.17 ppm. The urethane protons bound to nitrogen and N-BOC-amine (b, c) were confirmed at 4.85-5.25 ppm. The signal at 1.42 ppm was assigned to methyl protons in BOC.

linear without reaching plateau during the 14-week observation period post injection (FIG. 13). The release was more sustained at higher concentration because ESHU formed a more rigid gel at higher concentration. The half-life of free Avastin in eyes is on the order of 7 to 10 days. The window of therapeutic concentration most likely depends on local conditions, such as the presence of blood or fluid in the neovascular complex, and the state of the vitreous gel into which the drug is injected. Therefore, the Avastin-ESHU delivery system has three advantages over direct injection in that: 1. The therapeutic window is much longer, 2. The release is sustained, and 3. The injection frequency is greatly reduced.

Example 5

IKVAVS (SEQ ID NO: 21) Conjugated Reverse Thermal Gel Promotes Neurite Outgrowth Experimental Methods
Synthesis of Reverse Thermal Gel Reverse thermal gel was synthesized. N-BOC-serinol (0.5 g, 2.62 mmol) was dissolved in 1 ml anhydrous DMF in a 25 ml round bottom flask at 90° C. under a nitrogen atmosphere. HDI (0.44 g, 2.62 mmol) was added slowly and the polymerization was performed. After 48 h, HDI (22 mg, 0.131 mmol) was added to facilitate the reaction. The polymerization was performed for 2 days. More HDI (0.88 g, 5.24 mmol) was added and the reaction mixture was stirred for 12 h. After cooling down to ambient temperature, the mixture was precipitated in excess anhydrous diethyl ether. The polymer was dissolved again in 2 ml anhydrous chloroform and poured into excess anhydrous diethyl ether to precipitate out the polymer. The purification process was carried out twice and the precipitates were washed in 100 ml of anhydrous diethyl ether overnight to remove unreacted HDI. The intermediate was obtained after drying at 45° C. under vacuum. As synthesized intermediate (1 g) and PEG (3 g, Mw: 550) were dissolved in 2 ml anhydrous DMF in a 25 ml round bottom flask and the reaction was performed at 90° C. for 12 h under a nitrogen atmosphere. After cooling down, the mixture was precipitated into excess anhydrous diethyl ether. After drying, the polymer was further purified with dialysis membrane in water at room temperature for 3 days. The dialyzed solution was freeze-dried and a transparent reverse thermal gel was obtained.

Conjugation of IKVAVS (SEQ ID NO: 21)

De-protection of reverse thermal gel: As synthesized gel (100 mg) was dissolved in 10 ml chloroform in a 50 ml round bottom flask. TFA (10 ml) was added and BOC de-protection was performed for 1 h at room temperature. After removing TFA and chloroform by rotary evaporation, the polymer was purified using dialysis in water at room temperature for 2 days. The dialyzed solution was freeze-dried and a pale yellowish solid ($NH_2$-GEL) was obtained.

Synthesis of IKVAVS (SEQ ID NO: 21) Conjugated Reverse Thermal Gel (IKVAVS-GEL):

I(BOC)K(BOC)VAVS(tBu)-OH (83 mg, 0.095 mmol) was dissolved in 23 ml anhydrous DMF in a 50 ml round bottom flask. DCC (21.6 mg, 0.105 mmol) solution in 1 ml anhydrous DMF was added slowly at 0° C. $NH_2$-GEL (50 mg, 0.19 mmol $NH_2$) solution in 1 ml anhydrous DMF was added with a catalytic amount of DMAP, which was stirred for 24 h at room temperature under a nitrogen atmosphere. After 24 h, acetic anhydride (19.4 mg, 0.19 mmol) and pyridine (75.1 mg, 0.95 mmol) were added which was then stirred for 24 h at room temperature. The cyclohexylurea was filtered off. After removing 90% DMF using rotary evaporator, it was poured into excess diethyl ether to precipitate out I(BOC)K(BOC) VAVS(tBu)-GEL. After drying, BOC was removed in 20 ml chloroform/TFA (50/50, v/v) mixture for 1 h at room temperature. After removing TFA and chloroform using rotary evaporator, the polymer was purified by dialysis in water at room temperature for 2 days. The dialyzed solution was freeze-dried and a pale yellowish solid, IKVAVS-GEL, was obtained.

Cell Culture

Cells, SH-SY5Y (ATCC, CRL-2266), were cultured in DMEM/F12 (1:1) medium with 10% fetal bovine serum (FBS), and 1% antibiotics. The cells were incubated in a humidified atmosphere with 5% $CO_2$ at 37° C. The medium was refreshed every three days until the cells reached 95% confluence. The cells were harvested from the petri dish by incubation in 1 ml of trypsin solution (0.25%) for 5 min, neutralizing with 5 ml of serum-supplemented medium, centrifugation and removal of supernatant. The cell pellets were resuspended in serum-supplemented medium and $5 \times 10^3$ cells was used immediately for 2D neuronal cell culture.

2D Neuronal Cell Culture

Fifty µl of each solution (15%, wt) of pure reverse thermal gel and IKVAVS-GEL was transferred into 96-well plate on 37° C. heating plate. After 5 min, cell suspension ($5 \times 10^3$ cells) in 150 µl of medium was added on top of the gel. For a control, the same number of cell suspension in 200 µl of medium was transferred into laminin coated 96-well plate. A 100 µl of medium was refreshed every two days. The cell growth was examined on a microscope. After 7-day culture, 10 µM of retinoic acid (RA) was added and neurite outgrowth was monitored on a microscope.

Results
3D Structure of IKVAVS-GEL

Figure 14:
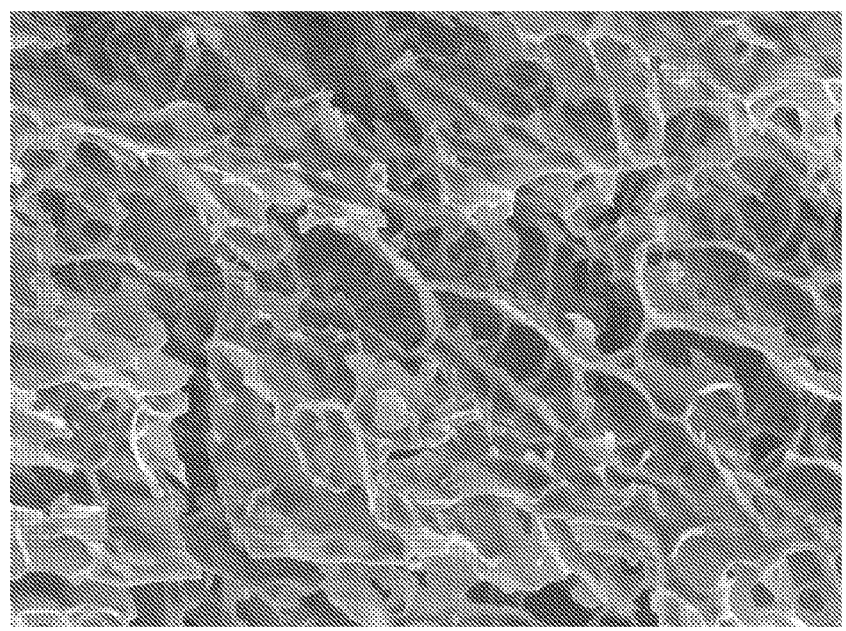
FIG. 14. 3D structure of IKVAVS-GEL.

To examine 3D structure of IKVAVS-GEL, 15% gel solution was placed in 37° C. water bath. Immediately after the gelation, it was placed in liquid nitrogen, frozen, and lyophilized. After drying, 3D structure was examined by SEM. Both the macro and micro pores were observed and they were interconnected each other (FIG. 14) which are good conditions for cell migration and nutrient supply.

2D Cell Growth and Neurite Outgrowth

Figure 15:
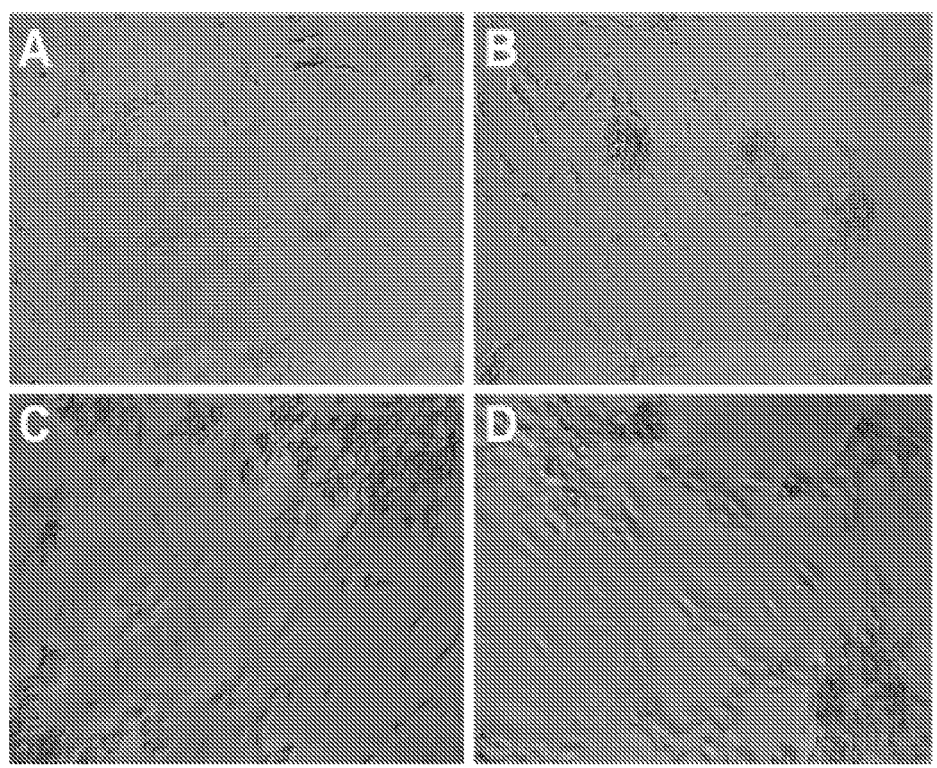
FIG. 15. Phase contrast of cell morphology and neurite outgrowth on laminin surface. (A) 1 day, (B) 7 days, (C) 14 days without RA, and (D) 14 days with RA. Images were taken by the magnification of 100× for (A) and (B), and 200× for (C) and (D).

Cells attached very well on laminin surface, a positive control, and few floating cells were observed (FIG. 15A). After 7-day culture, cells grew as clusters and formed many clumps which are typical morphology of growing SH-SY5Y (FIG. 15B). At day 7, 10 µM of RA (final concentration) was administered in one group and the differentiation of cells was compared after 14-day culture. Interestingly, some short neurite outgrowth was observed in a group without RA (FIG. 15C). However, much dense and longer neurite outgrowth was observed with RA (FIG. 15D).

Thus, laminin surface provided a good environment not only for cell growth but neurite outgrowth.

Figure 16:
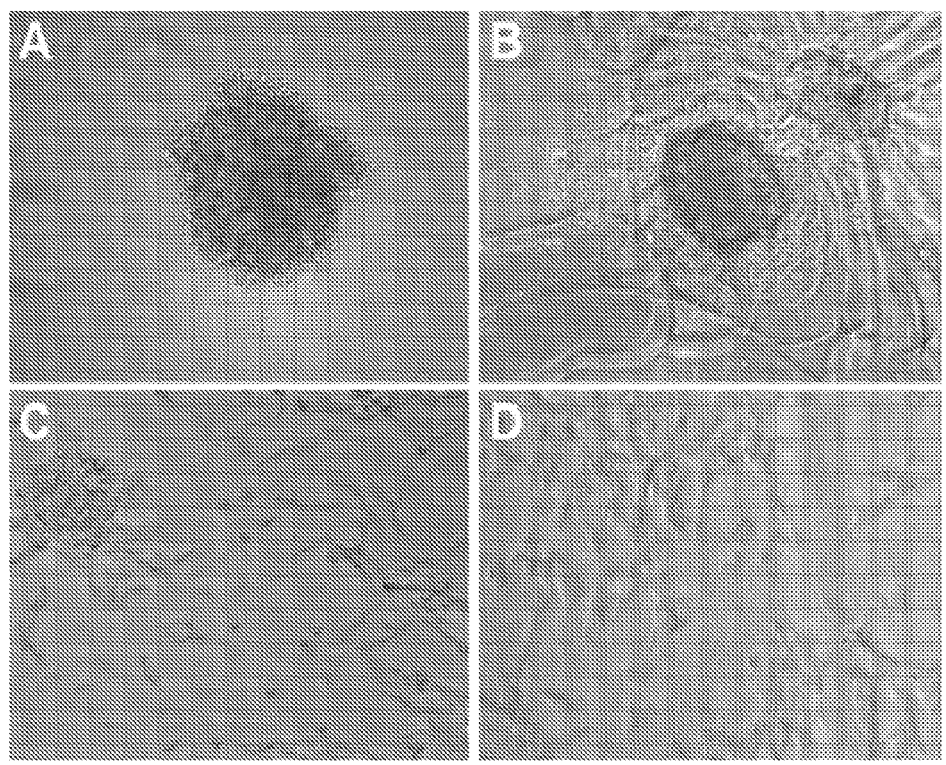
FIG. 16. Phase contrast of cell morphology and neurite outgrowth on pure reverse thermal gel surface. (A) 1 day, (B) 7 days, (C) 14 days without RA, and (D) 14 days with RA. Images were taken by the magnification of 100× for (A) and (B), and 200× for (C) and (D).
Figure 17:
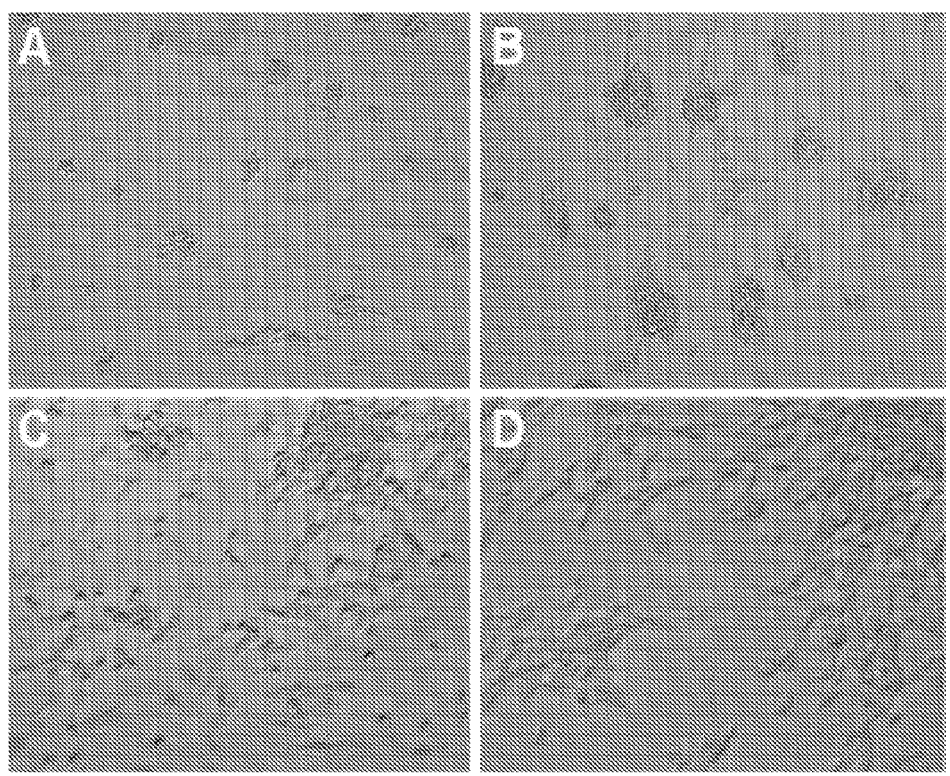
FIG. 17. Phase contrast of cell morphology and neurite outgrowth on IKVAVS-GEL surface. (A) 1 day, (B) 7 days, (C) 14 days without RA, and (D) 14 days with RA. Images were taken by the magnification of 100× for (A) and (B), and 200× for (C) and (D).

Cells seeded on pure reverse thermal gel did not attach well on the surface. Since the surface did not provide any bioactive cue, cells rather aggregated together (FIG. 16A) and slowly migrated from the aggregates (FIG. 16B). The differentiation was also not as extensive as the one on laminin surface. A few neurite outgrowth was observed without RA (FIG. 16C). And they were not extended well even with RA (FIG. 16D). Thus, pure reverse thermal gel surface did not seem to provide a good environment for cell attachment and neurite extension. On the contrary, cells seeded on IKVAVS-GEL surface showed as good morphology and neurite outgrowth as on laminin surface. Cells attached well on the surface and did not form a big aggregate as pure reverse thermal gel (FIG. 17A). They formed many clumps after 7-day culture as seen on laminin surface (FIG. 17B). Neurite outgrowth without (FIG. 17C)/with (FIG. 17D) RA were much better than that on pure reverse thermal gel which is comparable with laminin surface. Thus, IKVAVS (SEQ ID NO: 1) conjugated reverse thermal gel provided a good cue for cell attachment and promoted neurite outgrowth.

Example 6

Transplantation of IKVAVS (SEQ ID NO: 21) Conjugated Reverse Thermal Gel Promotes Axon Regeneration and Functional Recovery after a Thoracic Spinal Cord Contusion in Adult Rats Aim:

To determine the number of neurons with an axon projecting beyond a thoracic spinal cord contusion and hind limb motor performance after transplantation of IKVAVS (SEQ ID NO: 21) conjugated reverse thermal gel.

Hypotheses:

IKVAVS (SEQ ID NO: 21) conjugated reverse thermal gel promotes axonal regeneration in the contused adult rat spinal cord, and recovery of hindlimb motor function after a contusion of the rat thoracic spinal cord is proportional to the number of regenerated axons into the caudal cord.

Model:

IKVAVS (SEQ ID NO: 21)-conjugated reverse thermal gel is transplanted into a 3-day old contusion in the adult rat T9 spinal cord. Control rats receive ESHU or 'medium'. Survival is determined 1, 2, 4, and 8 weeks after transplantation. Biocompatibility, anatomical changes, cellular responses, axon regeneration, and motor function is investigated.

Methods

Rats:

Adult female Sprague Dawley, 180-200 g. Total number of rats is 63. Three groups are as follows: pure reverse thermal gel, IKVAVS (SEQ ID NO: 21) conjugated reverse thermal gel, and medium only, with 20 rats each (n=3 for 1, 2, and 4 weeks; n=12 for 8 (+1) weeks).

Contusion:

T9; 1H-impactor at 200 kDyn.

Implantation:

Five (5) μL pure reverse thermal gel, IKVAVS (SEQ ID NO: 21) conjugated reverse thermal gel, or medium into mid-point of 3-day old contusion.

Survival:

1, 2, 4, and 8 (+1 for tracing) weeks after transplantation.

Motor Testing:

Only in 8 (+1) week survival group. BBB (includes BBB-subscore) (before (3 times) and 1, 3 days after injury, and 3, 7 days, and then weekly after transplantation); foot print and horizontal ladder walking (before (3 times) and 3 days after injury, and 3 days and 1, 2, 4, 8 weeks after transplantation).

Retrograde Tracing:

At 8 weeks after transplantation, 1.2 μl 2% FB is injected in the spinal cord 7 mm caudal to the contusion epicenter.

Histology:

4% paraformaldehyde fixation. Cryostat sections of spinal cord (transplant plus 5 mm rostral and distal cord: 20 μm, horizontal, 10 series) and brainstem and cerebral cortex (40 μm, transversal, 10 series).

Analyses (*=Main Outcome Measures. Others are to Support)

Analysis of Axon Regeneration:
1. Quantify FB-labeled neurons in spinal cord rostral to transplant, brainstem, cortex.
*2. Quantify serotonergic and dopaminergic axons caudal to transplant.

Analysis of Motor Function:
*1. Overground locomotion (BBB)+higher motor functions (BBB subscore).
*2. Sensorimotor performance (horizontal ladder walking).
*3. Locomotion pattern: stride length, base of support, and angle of rotation (foot print).

Analysis of Cellular Changes:
1. Scar (ICC for astrocytes and CSPG)
2. Cell architecture (Nissl staining).
3. Neuron presence (ICC for NeuN)
4. Inflammation (ICC for macrophages)

Analysis of Anatomical Changes:
1, Tissue sparing (using Nissl-stained sections).

*=main outcome measures. Others are to support.

Example 7

Testing of Intraocular Dosage Form in Rabbits

Human eyes are often exposed to various risks of ocular diseases. They can be an age-related such as macular degeneration; virulent inflammations by foreign bodies such as endophthalmitis; and systemic side effects such as diabetic retinopathy, macular edema, and retinal vein occlusion. Intravitreal drug injections are the most effective way to maximize drug concentrations in the eye and reduce the loss whereas limiting systemic exposure. However, the effective management of chronic ocular conditions requires long-term frequent local administrations with over- and underdoses. Those repeated intravitreal injections are not only invasive and inconvenient for patients, but they may also greatly increase the risk of complications such as intraocular pressure elevation, cataracts, and retinal detachment.

To overcome these drawbacks therapeutic agents are conjugated with reverse thermal gels (TA-ESHU) which undergo temperature triggered sol-gel phase transition and form a gel at body temperature. Since the TA-ESHU can form gels by a simple injection in the vicinity of target area, the loss of therapeutic agents can be minimized. The controlled release sustains the vitreous concentration of the therapeutic agents in the therapeutic range longer with reduced side effects and treatment frequency achieving higher therapeutic index. The release rate is controlled by varying the affinity between the gel and the therapeutic agents. The density of the delivery system is designed to approximately match that of the vitreous fluid.

Sample sizes are selected based on a power analysis with a significance level a of 0.05 and a power $(1-\beta)$ of 0.85. Assuming a typical standard deviation of 35% and desiring to detect a 33% difference in means, we obtain a sample size of 10 using MiniTab (Statistical Software). In case our standard deviation assumption is proven to be invalid a posteriori, we will employ an adaptive sampling rate for the testing.

Therapeutic agent-conjugated polymer compositions are injected in three separate parts of the animal's eye, upper back, and lower back. Each part has two samples. For eye, a left eye and a right eye. For upper back, a left side and a right side. For lower back, a left side and a right side. Then each animal has two samples for the biocompatibility and biodegradibility. Five animals are used for each time point. Then, the sample size in each time point is 10 (5×2=10).

Preparation:

All rabbits are used after at least three days post arrival. For each group of experiment: 5 survival times×6 rabbits/survival time (5 for test, 1 for control)=30 rabbits.

Pre-Operative Evaluation and Preparation:

Pre-op evaluation and preparation includes weighing the rabbit and recording the body weight.

For Biocompatibility Experiment Through Intravitreal Injection:

0.05 ml of 20% and 30% therapeutic agent-conjugated reverse thermal gel solution will be injected in the eye. In one example, the therapeutic agent is Avastin. Typically the injection of thermal gel has been done under anesthesia condition for intravitreal injection. Rabbits are anesthetized using either sodium pentobarbital or a mixture of ketamine and xylazine. The volume of thermal gel for intravitreal injection has been in the range of 50-100 µl. The minimum volume (50 µl) is injected. A 25 gauge needle is used for the injections. After euthanization with 120 mg/kg sodium pentobarbital at 1, 3, 7, 14 and 30 days, the surgical eye including the upper eyelids are removed. The surgical eye is fixed in 4% formaldehyde, stained, and examined by standard histological analysis for any signs of acute and chronic inflammation. Control is 0.05 ml of saline solution.

For Intraocular Pressure (IOP) Measurement:

The measurement of IOP is performed preinjection and at 1, 3, 7, 14 and 30 days post-injection using tonometer by distributor's protocol.

At the end of the experiments cells are isolated for future biocompatibility and stromal cell differentiation capability tests of therapeutic agent-conjugated reverse thermal gels as follows.

Animals are euthanized following survival times and tissue and cells are harvested.

The rabbits are examined and its response to gentle palpation or handling of any presumed painful areas (e.g., the site of surgery) is assessed. The rabbit is weighed every 24 hours, and the cage is examined for signs of normal or abnormal urination or defection.

The following criteria will be sued to determine full recovery from surgery: 1) locomotive and grooming behavior equivalent to presurgical state, and 2) eating and drinking equivalent to presurgical state. Postoperative analgesia will be provided by injections of Ketoprofen 12 hours after surgery, and once per two days afterward (if needed). Rabbits will be monitored closely (every 12 hours) for any signs of distress (vocalization, decrease in food consumption, etc.). If rabbits scratch or bite their injection sites, if the skin becomes reddened or if dermatitis develops, or rabbits lose more than 20% of their immediate post-operative body weight, they will be euthanized. Body weight will be monitored every 24 hours.

For intravitreal injection, some clinical signs may appear when animals receive injections, such as scratching their injection sites, increase in intraocular pressure, weight loss. Complications are not expected in any case. If rabbits keep scratching their intravitreal injection sites, if the intraocular pressure keeps increasing, or rabbits lose more than 20% of their immediate post-operative body weight, they are euthanized. Body weight is monitored every 24 hours.

Example 8

Spinal Cord Injury

A. Transection

To determine the reverse thermal gels' efficacy in functional nerve regeneration, 10 rats per time point are used because this is the minimum number needed in order to obtain meaningful data. Histological, behavioral, and electrophysiological assessment is performed at 2, 5, and 8 weeks for spinal cord regeneration after surgery. If 10 animals are used per condition, then 30 animals are necessary to fulfill the study (3×10=30). 10 rats are used per condition. Power analysis is performed using MiniTab Software (Statistical Software). Ten types of polymer composition are tested, so 300 animals are necessary to fulfill the study (10×30=300).

Negative control is "injury only" for CNS nerve regeneration. Positive controls are not appropriate for the following reasons. There is no current treatment that can lead to functional recovery, so there is no positive control. Therefore, two groups of 20 rats in total are required for the first time experiment, therefore 320 animals are necessary to fulfill the study (10×30+20=320). A total of 60 animals (three time points, 10 animals/time point) for each polymer conduit will be sacrificed at three time points for histological, behavioral, and electrophysiological assessment on nerve regeneration.

Preparation:

All animal are used after at least three days post arrival. The animals are prepared by removing hair from the surgical site, and the surgical sites are sterilized with an appropriate skin disinfectant such as Betadine. For each experiment: three survival times×10 animals/survival time are used, totaling 30 animals. Pre-operative evaluation and preparation includes weighing the animal and recording the body weight. Aseptic surgical technique is ensured by performing the surgeries in a disinfected suite.

For Direct Spinal Cord Injury:

1. The rats are anesthetized using sodium pentobarbital (45-50 mg/kg) given either intraperitoneally (using a 25-26 gauge needle) under brief anesthesia induced with 5% isofluorane.
2. Opthalmic ointment is used on the eyes to prevent corneal abrasion.
3. The hair down the back over the spine is removed with electric clippers.
4. The area is cleaned with chlorhexaderm and then with 70% ethanol.
5. The rat is draped with sterile surgical drapes.
6. An incision is made over the thoracic region of the spinal cord T6-T11.
7. The muscle is cut on both sides of the spine.
8. A double laminectomy is performed removing T9 and T10.
9. The dura mater is excised longitudinally.
10. To sever the dorsal corticospinal tracts, microscissors previously marked at 1.5 millimeters are used to cut down through the dorsal columns until we reach the pre-determined depth. The length of the cavity is 2 millimeters.
11. The reverse thermal gel is injected into the lesioned cavity.
12. In order to stop bleeding during surgery, Tisseel Fibrin Sealant, a product made by Baxter, is applied. It is sterile and non-pyrogenic. The literature contains many references to the use of this product in rats indicating that it is safe and effective in this species. Tisseel is mixed according to package directions and applied topically to bleeding areas during surgery. No side effects are expected.
13. The dura is sutured and the muscle and skin will be closed in layers.
14. The rat recovers on a heating pad or under a heat lamp.
15. Animals are monitored for up to 8 weeks. These rats are expected to maintain the ability to urinate and defecate on their own without having a person manually express on the rats also are expected to be able to walk around on their fore and hind limbs on their own accord; however, in the first 48 hours, they are expected to go through spinal shock and should not be able to have full use of their hind limbs.

16. Ketaprofen is administered post-operatively for pain that the rat may experience if needed.
17. Suture and/or wound clips are removed 10-14 days post-operatively).

Rodent Euthanasia and Tissue Harvest:

Following post-inoculation survival times of each time point, the animals are be anesthetized with 50 mg/kg sodium pentobarbital intraperitoneally, and tissue is harvested and transfer into buffered aldehyde solution. Tissue will be harvested after complete euthanasia.

B. Compression

Alternately, another spinal cord injury model is performed according to this protocol. No other change is made to this protocol. In the original protocol, we will use transection to create spinal cord injury. Here, we describe an alternative spinal cord injury model to transection: a clip compression method is used to create spinal cord injury as the second model in the protocol. Because the "transection procedure" is expected to cause more severe injury to spinal cord as compared with "compression injury model", we evaluate the effect of polymers through "compression injury model" at first, then two of the most effective polymers are chosen for the evaluation in "transection model". Like the first protocol, three time points are set, with ten rats per time point, totaling 60 rats for this modified protocol.

In the surgical procedure, a 30-40 mm dorsal midline incision is made and laminectomy is performed at T6-T11 level. Compressive injury is produced by transient extradural application of a modified iris clip, which exerted a force of about 90 gram on the spinal cord for 2 min. After removal of the clip, the dura in the lesion area is incised, and spinal cord is exposed, then the prepared polymer is administered in the lesion. Dura and skin incision is closed, and the animal is returned to cages with highly absorbent soft bedding in pairs (to reduce isolation-induced stress).

No particular animal injury model of human spinal cord injury completely mimics all clinical aspects of human patients. The use of multiple injury models has greatly advanced our understanding of the pathophysiology, so we use both the transection method because it causes 100% nerve damage and should be more controllable in terms of nerve damage than partial injury model such as contusion or compression. However, transection injury method is very different from most of clinical SCI cases. Most SCI cases are caused by automobile and sports accidents, and gunshot wounds. Contusion and compression injury models more closely mimic the conditions in these clinical cases. Of contusion and compression models, the latter may be preferred because it is quicker and simpler to apply.

Immediately following surgery and during recovery from anesthesia, rats recover under a heat lamp to raise the recovery area ambient temperature to between 85-90° F. Each animal is examined and assessed for its response to gentle palpation or handling of any presumed painful areas (e.g., the site of surgery, the site of lesion). The animal is weighed every 24 hours, and the cage is examined for signs of normal or abnormal urination or defection.

The following criteria is used to determine full recovery from surgery: 1) locomotive and grooming behavior equivalent to presurgical state, and 2) eating and drinking equivalent to presurgical state. Postoperative analgesia is provided by injections of Ketoprofen 12 hours after surgery, and once per two days afterward. Animals are monitored closely (every 12 hours) for any signs of distress (vocalization, decrease in food consumption, etc.). Furthermore, the health of the animals following surgery is monitored for adverse signs due to the effects of the injured nerves. If rats scratch or bite their implants, if they lose hair over their implants, if the skin becomes reddened or if dermatitis develops, if incisions do not heal or an exudate develops or rats lose more than 20% of their immediate post-operative body weight, they are euthanized.

Having described this invention, it will be understood to those of ordinary skill in the art that the same can be performed within a wide and equivalent range of conditions, formulations and other parameters without affecting the scope of the invention or any embodiment thereof.

We claim:

1. A reverse thermal gel composition comprising a triblock copolymer, or a pharmaceutically acceptable salt thereof, having the structure B-A-B in which A is one of a polyurethane or poly(ester urethane) group that comprises one or more pendant amine groups, blocked amine groups or active agents and B is a hydrophilic block, wherein the composition is a gel at 35° C.-40° C. and a liquid solution at a lower temperature, and wherein A is a copolymer of a diol and a diisocyanate.

2. The composition of claim 1 in which the diol is an amino-substituted or N-substituted serinol in which the N is substituted with one of a hydrogen, a protective group, or an active agent.

3. The composition of claim 2 in which the N of the N-substituted serinol is —NHR in which R is a protective group.

4. The composition of claim 3 in which R is selected from the group consisting of carbobenzyloxy; p-methoxybenzyl carbonyl; tert-butyloxycarbonyl; 9-fluorenylmethyloxycarbonyl; benzyl; p-methoxybenzyl; 3,4-dimethoxybenzyl; p-methoxyphenyl; tosyl; nosyl (4-nitrobenzenesulfonyl) and 2-nitrobenzenesulfonyl.

5. The composition of claim 3 in which R is tert-butyloxycarbonyl.

6. The composition of claim 1 in which the diol comprises one or more ester groups.

7. The composition of claim 6 in which the diol is a reaction product of a cyclic anhydride and a diol comprising one or more pendant active groups, blocked active groups or active agents.

8. The composition of claim 7 in which the diol is the reaction product of succinic anhydride and the diol is an N-substituted serinol in which the N is substituted with one of a hydrogen, a protective group, or an active agent.

9. The composition of claim 1 in which the diol comprises a pendant amino group or an amine.

10. The composition of claim 1, in which the diisocyanate is hexamethylene diisocyanate (1,6-diisocyanatohexane).

11. The composition of claim 1, comprising a copolymer comprising the structure:

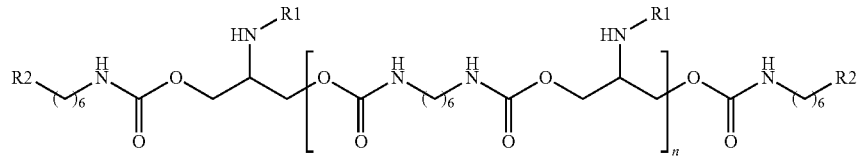

in which R1 is H or a protective group, R2 is isocyanate or —NC(O)-polyethylene glycol (—NC(O)-PEG) and n is greater than 5.

12. The composition of claim 1, comprising a copolymer comprising the structure:

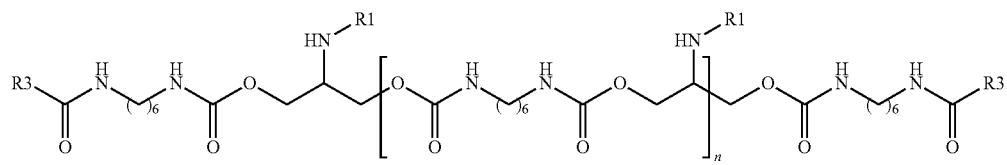

in which R1 is H or a protective group, R3 is PEG and n is greater than 5.

13. The composition of claim 1, comprising a copolymer comprising the structure:

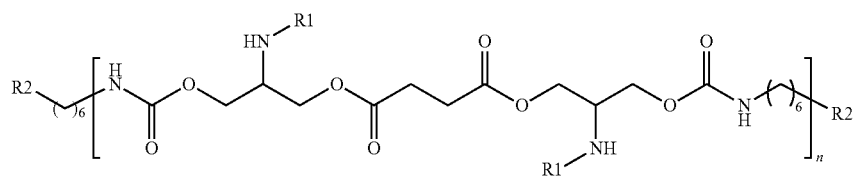

in which R1 is H or a protective group or an active agent, R2 is isocyanate or —NC(O)-PEG and n is greater than 5.

14. The composition of claim 1, comprising a copolymer comprising the structure:

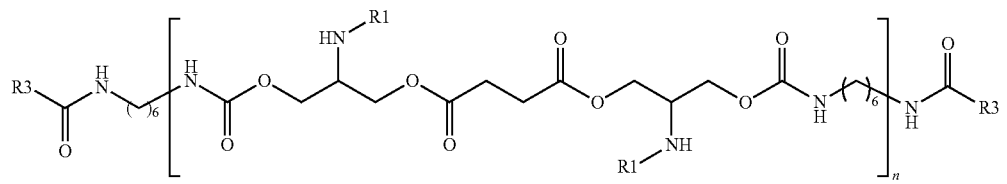

in which R1 is H or a protective group, R3 is PEG and n is greater than 5.

15. The composition of claim 1, the triblock copolymer having an average molecular weight of between about 5,000 and 10,000 Da (Daltons), excluding, when present, the molecular weight of the active agent.

16. The composition of claim 1 in which A is one of a polyurethane or poly(ester urethane) group that comprises one or more pendant charged or active groups.

17. The composition of claim 16 in which the one or more pendant charged or active groups is —NH$_2$.

18. The composition of claim 17 in which the NH$_2$ is covalently linked or non-covalently bound to one or more active agents or biologically functional groups.

19. The composition of claim 17 in which the NH$_2$ is linked to an extracellular matrix (ECM) epitope.

20. The composition of claim 17 in which the NH$_2$ is linked to a functional entity that aids in evasion of an immune response.

21. The composition of claim 1 in which the active agent is an oligopeptide selected from the group consisting of IKLLI (SEQ ID NO: 1), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11), PDSGR (SEQ ID NO: 12), RNIAEIIKDI (SEQ ID NO: 13), DGEA (SEQ ID NO: 14), VTXG (SEQ ID NO: 15), PRRARV (SEQ ID NO: 16), YEKPGSPPREVVPRPRPGV (SEQ ID NO: 17), RPSLAKKQRFRHRNRKGYRSQRGH-SRGR (SEQ ID NO: 18), RIQNLLKITNLRIKFVK (SEQ ID NO: 19), RGD, IKVAV (SEQ ID NO: 20) and IKVAVS (SEQ ID NO: 21).

22. The composition of claim 1 further comprising an active agent complexed to the triblock copolymer.

23. The composition of claim 22, in which the active agent is one of bevacizumab, pegaptanib sodium and Ranibizumab.

24. The composition of claim 22 in which the active agent is one or more of an antibiotic, an anti-inflammatory agent, an antiangiogenic agent, a hormone, a cytokine, a chemokine, and a growth factor.

25. The composition of claim 22 in which the active agent is chosen from one or more of: pegaptanib sodium; lucentis; tryptophanyl-tRNA synthetase (TrpRS); AdPEDF; VEGF TRAP-EYE; AG-013958; bevacizumab; JSM6427; TG100801; ATG3; perceiva; E10030; ARC1905; colociximab; endostatin; vatalanib; pazopanib; sirolimus; bevasiranib; AGN211745; nepafenac; ketorolac tromethamine; acetaminophen; bromfenac; ciprofloxacin; norfloxacin; afloxacin; levofloxacin; gentamicin; tobramycin; neomycin; erythromycin; trimethoprim sulphate; polymixin B; ganciclovir and fomivirsen.

26. The composition of claim 1, in which the triblock copolymer is one of:

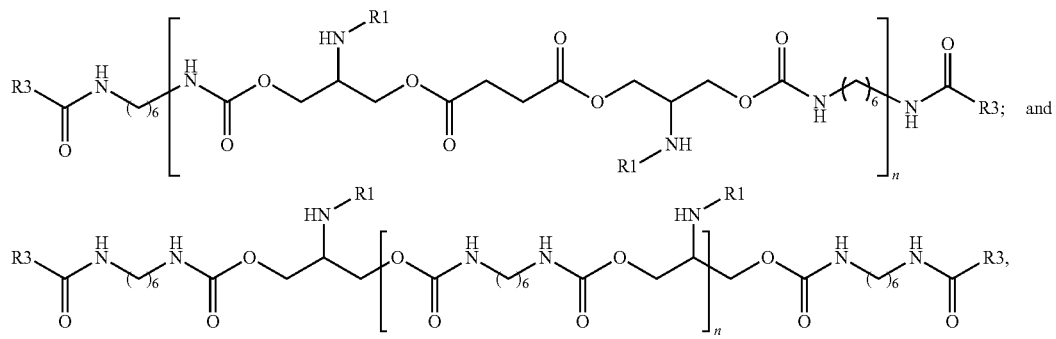

in which R1 is H and R3 is PEG, complexed with an antiangiogenic agent.

27. The composition of claim 26 in which the antiangiogenic agent is one of bevacizumab and pegaptanib sodium.

28. The composition of claim 1 in which B is selected from the group consisting of PEG; hyaluronan; poly(vinyl alcohol); oligo(vinyl alcohol); a poly(electrolyte); an oligo(electrolyte); and a polycarbohydrate.

29. The composition of claim 1 in which B is a polyethylene glycol.

30. A method of delivering an active agent to a patient, comprising delivering to the patient a reverse thermal gel composition comprising an active agent and a triblock copolymer having the structure B-A-B in which A is one of a polyurethane or poly(ester urethane) group that comprises one or more pendant amine groups, blocked amine groups or active agents and B is a hydrophilic block and the composition is a gel at 37° C. and a liquid at a lower temperature, wherein A is a copolymer of a diol and a diisocyanate.

31. The method of claim 30 in which the active agent is one or more of an antibiotic, an anti-inflammatory agent, an antiangiogenic agent, a hormone, a cytokine, a chemokine and a growth factor.

32. The method of claim 30 in which the active agent is chosen from one or more of: pegaptanib sodium; lucentis; tryptophanyl-tRNA synthetase (TrpRS); AdPEDF; VEGF TRAP-EYE; AG-013958; bevacizumab; JSM6427; TG100801; ATG3; perceiva; E10030; ARC1905; colociximab; endostatin; vatalanib; pazopanib; sirolimus; bevasiranib; AGN211745; nepafenac; ketorolac tromethamine; acetaminophen; bromfenac; ciprofloxacin; norfloxacin; afloxacin; levofloxacin; gentamicin; tobramycin; neomycin; erythromycin; trimethoprim sulphate; polymixin B; ganciclovir and fomivirsen.

33. The method of claim 30, in which the composition is delivered to a patient's eye.

* * * * *

UNITED STATES PATENT AND TRADEMARK OFFICE
CERTIFICATE OF CORRECTION

PATENT NO. : 9,132,199 B2
APPLICATION NO. : 13/581518
DATED : September 15, 2015
INVENTOR(S) : Thomas Richard Friberg et al.

Page 1 of 1

It is certified that error appears in the above-identified patent and that said Letters Patent is hereby corrected as shown below:

IN THE SPECIFICATION

Column 8, Line 48, delete "afloxacin," and insert -- ofloxacin, --

Column 8, Lines 54-55, delete "polymixin" and insert -- polymyxin --

Column 9, Line 52, delete "colociximab" and insert -- volociximab --

Column 10, Line 36, delete "afloxacin," and insert -- ofloxacin, --

Column 10, Line 38, delete "polymixin" and insert -- polymyxin --

Column 23, Line 36, delete "sued" and insert -- used --

IN THE CLAIMS

Column 36, Lines 2-3, Claim 25, delete "colociximab;" and insert -- volociximab; --

Column 36, Line 6, Claim 25, delete "afloxacin;" and insert -- ofloxacin; --

Column 36, Line 7, Claim 25, delete "polymixin" and insert -- polymyxin --

Column 36, Lines 55-56, Claim 32, delete "colociximab" and insert -- volociximab --

Column 36, Line 59, Claim 32, delete "afloxacin;" and insert -- ofloxacin; --

Column 36, Line 60, Claim 32, delete "polymixin" and insert -- polymyxin --

Signed and Sealed this
Sixteenth Day of February, 2016

Michelle K. Lee
*Director of the United States Patent and Trademark Office*